US012599142B2

(12) United States Patent
Harashima et al.

(10) Patent No.: US 12,599,142 B2
(45) Date of Patent: Apr. 14, 2026

(54) BACTERIOPHAGE, BACTERIAL WILT DISEASE CONTROL AGENT, AND BACTERIAL WILT DISEASE CONTROL METHOD

(71) Applicant: PANEFRI INDUSTRIAL CO., LTD., Nagaokakyo (JP)

(72) Inventors: Toshiaki Harashima, Okinawa (JP); Kazuma Nakano, Okinawa (JP); Toru Karimata, Okinawa (JP); Kumiko Hokama, Okinawa (JP)

(73) Assignee: PANEFRI INDUSTRIAL CO., LTD., Nagaokakyo (JP)

( * ) Notice: Subject to any disclaimer, the term of this patent is extended or adjusted under 35 U.S.C. 154(b) by 552 days.

(21) Appl. No.: 18/007,432

(22) PCT Filed: Jul. 30, 2020

(86) PCT No.: PCT/JP2020/029189
§ 371 (c)(1),
(2) Date: Jan. 30, 2023

(87) PCT Pub. No.: WO2022/024287
PCT Pub. Date: Feb. 3, 2022

(65) Prior Publication Data
US 2025/0185668 A1     Jun. 12, 2025

(51) Int. Cl.
*A01N 63/40*     (2020.01)
*A01P 1/00*     (2006.01)
*C07K 14/005*     (2006.01)
*C07K 14/01*     (2006.01)
*C12N 7/00*     (2006.01)

(52) U.S. Cl.
CPC ............... *A01N 63/40* (2020.01); *A01P 1/00* (2021.08); *C07K 14/005* (2013.01); *C12N 7/00* (2013.01); *C12N 2795/10221* (2013.01); *C12N 2795/10222* (2013.01); *C12N 2795/10232* (2013.01); *C12N 2795/10271* (2013.01)

(58) Field of Classification Search
CPC ... A01N 63/40; A01P 1/00; A01P 3/00; C07K 14/005; C07K 14/01; C12N 7/00; C12N 2795/10221; C12N 2795/10222; C12N 2795/10232; C12N 2795/10271
See application file for complete search history.

(56) References Cited

U.S. PATENT DOCUMENTS

2014/0044679 A1     2/2014   Yamada et al.

FOREIGN PATENT DOCUMENTS

| JP | 2007-252351 A | 10/2007 |
| JP | 2012-231731 A | 11/2012 |
| JP | 2018-24589 A | 2/2018 |
| WO | WO 2017/104347 A1 | 6/2017 |

OTHER PUBLICATIONS

Zinke M. et al., "Major Tail Proteins of Bacteriophages of the Order Caudovirales", J. Biol. Chem. (2022), vol. 298, No. 1; pp. 101472 (total pp. 1-16). (Year: 2022).*
International Search Report issued Oct. 6, 2020 in PCT/JP2020/029189 filed Jul. 30, 2020, citing documents 1, 16-18 and 24-25 therein, 3 pages.
Su et al., "Complete Genome Sequence of a Novel Lytic Bacteriophage Isolated from Ralstonia Solanacearum", Arch Virol., 2017, 5 pages.
Putative Phage Tail Fiber Protein [Ralstonia Phage RSJ5], GenBank [online], 2014, [retrieved on Sep. 23, 2020], Internet: https://www.ncbi.nlm.nih.gov/protein/BAP34930.1/, 1 page.

* cited by examiner

*Primary Examiner* — Satyendra K Singh
(74) *Attorney, Agent, or Firm* — Oblon, McClelland, Maier & Neustadt, L.L.P.

(57)     ABSTRACT

Bacteriophages that comprise a tail fiber protein sequence comprising a C terminus host recognition site described by SEQ ID NO: 1 and which infect *Ralstonia solanacearum* which causes bacterial wilt disease are disclosed. Compositions comprising these bacteriophages may be employed as wilt control agents. Methods for preventing or treating diseases caused by *Ralstonia solanacearum* such as bacterial wilt disease are also disclosed. A bacterial wilt disease control method in a plant may include administering such bacteriophages to a plant or to a plant growth medium and can be effective against a wide variety of *Ralstonia solanacearum* strains. Nucleic acids encoding the C terminus host recognition site and amino acid sequences comprising the host recognition site are also disclosed.

20 Claims, 4 Drawing Sheets

Specification includes a Sequence Listing.

SEQUENCE LISTING

<160> NUMBER OF SEQ ID NOS: 3

<210> SEQ ID NO 1
<211> LENGTH: 551
<212> TYPE: PRT
<213> ORGANISM: Unknown
<220> FEATURE:
<221> NAME/KEY: MISC_FEATURE
<223> OTHER INFORMATION: Bacteriophage RKP181 host recognition domain
      containing C-terminus of the tail fiber protein

<400> SEQUENCE: 1

Lys Thr Trp Arg Asp Glu Thr Leu Thr Ala Arg Asp Ala Thr Phe Thr
1               5                   10                  15

Ala Arg Asp Thr Thr Leu Gly Tyr Arg Asp Thr Thr Leu Thr Tyr Lys
            20                  25                  30

Asn Ala Ala Glu Ala Ala Arg Asp Ala Gly Phe Ala Ala Arg Asp Val
        35                  40                  45

Ala Leu Ala Ala Arg Asp Thr Thr Leu Gly Tyr Arg Asp Thr Ala Asn
    50                  55                  60

Gln His Arg Ile Asp Ala Gln Ala Ala Arg Asp Leu Ala Leu Gln Tyr
65                  70                  75                  80

Arg Asn Glu Ala Glu Ala Phe Lys Asn Thr Ala Ser Asp Lys Ala Asp
                85                  90                  95

Ile Val Leu Thr Ile Glu Ala Thr Ala Asn Ser Ala Lys Ala Glu Ala
            100                 105                 110

Gln Ala Ala Thr Ala Ala Thr Thr Gly Leu Met Asp Asn Asp Leu Gln
            115                 120                 125

Leu Phe Val Asn Gly Thr Gln Arg Arg Asp Ile Lys Val Lys Ala Gly
    130                 135                 140

Lys His Asp Ala Gln Gly Val Gln Arg Ala Gly Val Arg Phe Thr Asp
145                 150                 155                 160

Val Asp Thr Ile Ala Val Glu Arg Tyr Asn Gln Thr Thr Gly Val Ile
                165                 170                 175

Ile Asp Thr Pro Val Lys Ile Asp Gln Ala Thr Gly Asp Val Val Leu
            180                 185                 190

Ala Ser Lys Lys Ile Lys Gly Val Thr Thr Pro Thr Ala Asn Asp Glu
            195                 200                 205

Ala Ala Asn Lys Ser Tyr Ala Asp Thr Lys Leu Pro Phe Val Gly Gly
    210                 215                 220

Thr Leu Thr Gly Ser Leu Phe Val Ser Gly Ala Thr Asp Asn Ala Gly
225                 230                 235                 240

Ala Phe Arg Val Thr Ala Asp Leu Gly Gly Ala Trp Val Asp Trp Asn
            245                 250                 255

Ala Ala Arg Lys Tyr Pro Leu Gln Ile Asp Cys Pro Ala Ser Ser Ala
            260                 265                 270

Ala Tyr Gly Gly Ile Arg Trp Thr Arg Trp Gly Ala Arg His Ile Ala
        275                 280                 285

Ala Ile Asp Ala Phe Asp Asn Thr Gly Gly Ala Pro Val Ile Val Met
    290                 295                 300

His Leu Gly Asp Gln Asn Asn Ala Trp Ser Phe Tyr Lys Asp Asn Ile
305                 310                 315                 320

Tyr Arg Gly Tyr Asn Gly Gly Tyr Val Trp Gly Ser Trp Asn Phe Asn
            325                 330                 335

Pro Ala Ser Lys Ala Asn Ala Asp Trp Ile Thr Asp Val Gly Ile Glu
            340                 345                 350

-continued

```
Gly Asn Asp Ile Arg Arg Pro Tyr Val Arg Arg Ala Ser Asp Gly Tyr
        355                 360                 365

Ile Val Arg Met Pro Arg Asn Phe Ser Gly Asn Ala Leu Glu Val Gly
        370                 375                 380

Trp Asp Gly Gly Leu Arg Trp Tyr Val Asp Gly Val His Gln Gly Ala
385                 390                 395                 400

Met Val Ser Asp Thr Asn Trp Arg Gly Ala Phe His Asn Asp Ala Gly
                405                 410                 415

Arg Ile Gly Arg Gly Gly Asp Trp Ser Ile Gly Asn Gly Tyr Phe Asp
                420                 425                 430

Val Val Ile Asp Gly Val Ser Tyr Gly Val Pro Phe Asn Pro Ser Asp
                435                 440                 445

Ala Arg Arg Lys Glu Asn Ile Val Pro Ser Thr Glu Asp Ala Ile Glu
        450                 455                 460

Lys Val Lys Gln Ile Lys Phe Tyr Ser Phe Asn Phe Lys Ala Asp Gly
465                 470                 475                 480

Leu Met Asp Ser Lys Lys Val His Gln Thr Gly Phe Ile Ala Gln Gln
                485                 490                 495

Leu Gln Gly Val Asp Pro Ala Leu Val Ile Gly Asp Asp Asn Pro Asp
                500                 505                 510

Met Thr Leu Ser Pro Asp Val Asn Ser Leu Leu Ser Leu Ala Leu Lys
                515                 520                 525

Ser Ile Gln Gln Leu Asp Ala Lys Ile Ala Val Leu Glu Glu Thr Ile
        530                 535                 540

Leu Ala Leu Lys Gly Asn Pro
545                 550
```

```
<210> SEQ ID NO 2
<211> LENGTH: 711
<212> TYPE: PRT
<213> ORGANISM: Unknown
<220> FEATURE:
<221> NAME/KEY: MISC_FEATURE
<223> OTHER INFORMATION: Bacteriophage RKP181 host recognition domain
      containing C-terminus of the tail fiber protein
<220> FEATURE:
<221> NAME/KEY: MISC_FEATURE
<222> LOCATION: (1)..(148)
<223> OTHER INFORMATION: a domain corresponding to the T7
      tail-attachment domain
<220> FEATURE:
<221> NAME/KEY: MISC_FEATURE
<222> LOCATION: (161)..(711)
<223> OTHER INFORMATION: the host recognition domain containing
      C-terminus

<400> SEQUENCE: 2

Met Ala Ala Pro Thr Thr Val Lys Val Tyr Pro Leu Asn Asn Val Val
1               5                   10                  15

Lys Asp Phe Pro Ile Asp Phe Asp Tyr Leu Ala Arg Glu Phe Val Val
                20                  25                  30

Val Thr Leu Leu Gly Asn Gly Arg Arg Glu Leu Val Gln Asn Ser Glu
        35                  40                  45

Tyr Thr Phe Leu Ser Ala Thr Gln Ile Arg Thr Thr Ala Thr Trp Gly
        50                  55                  60

Pro Ala Gln Gly Tyr Asp Asn Ile Glu Val Arg Arg Val Thr Ser Ala
65                  70                  75                  80

Glu Asn Arg Leu Val Thr Phe Asn Asp Ala Ser Ile Leu Arg Ala Ala
                85                  90                  95
```

-continued

```
Asp Leu Asn Leu Ala Glu Leu Gln Thr Val His Ile Ala Gln Glu Ala
        100             105             110

Arg Asp Leu Val Ser Asp Ala Leu Gly Thr Asn Asp Asp Gly Asn Leu
        115             120             125

Asp Ala Arg Asn Arg Arg Ile Val Asn Leu Gly Asn Pro Val Asp Pro
        130             135             140

Gln Asp Ala Met Thr Lys Asp Tyr Tyr Asp Ser Arg Leu Gly Glu Ala
145             150             155             160

Lys Thr Trp Arg Asp Glu Thr Leu Thr Ala Arg Asp Ala Thr Phe Thr
                165             170             175

Ala Arg Asp Thr Thr Leu Gly Tyr Arg Asp Thr Thr Leu Thr Tyr Lys
                180             185             190

Asn Ala Ala Glu Ala Ala Arg Asp Ala Gly Phe Ala Ala Arg Asp Val
            195             200             205

Ala Leu Ala Ala Arg Asp Thr Thr Leu Gly Tyr Arg Asp Thr Ala Asn
        210             215             220

Gln His Arg Ile Asp Ala Gln Ala Ala Arg Asp Leu Ala Leu Gln Tyr
225             230             235             240

Arg Asn Glu Ala Glu Ala Phe Lys Asn Thr Ala Ser Asp Lys Ala Asp
            245             250             255

Ile Val Leu Thr Ile Glu Ala Thr Ala Asn Ser Ala Lys Ala Glu Ala
            260             265             270

Gln Ala Ala Thr Ala Ala Thr Thr Gly Leu Met Asp Asn Asp Leu Gln
        275             280             285

Leu Phe Val Asn Gly Thr Gln Arg Arg Asp Ile Lys Val Lys Ala Gly
        290             295             300

Lys His Asp Ala Gln Gly Val Gln Arg Ala Gly Val Arg Phe Thr Asp
305             310             315             320

Val Asp Thr Ile Ala Val Glu Arg Tyr Asn Gln Thr Thr Gly Val Ile
            325             330             335

Ile Asp Thr Pro Val Lys Ile Asp Gln Ala Thr Gly Asp Val Val Leu
            340             345             350

Ala Ser Lys Lys Ile Lys Gly Val Thr Thr Pro Thr Ala Asn Asp Glu
        355             360             365

Ala Ala Asn Lys Ser Tyr Ala Asp Thr Lys Leu Pro Phe Val Gly Gly
        370             375             380

Thr Leu Thr Gly Ser Leu Phe Val Ser Gly Ala Thr Asp Asn Ala Gly
385             390             395             400

Ala Phe Arg Val Thr Ala Asp Leu Gly Gly Ala Trp Val Asp Trp Asn
                405             410             415

Ala Ala Arg Lys Tyr Pro Leu Gln Ile Asp Cys Pro Ala Ser Ser Ala
                420             425             430

Ala Tyr Gly Gly Ile Arg Trp Thr Arg Trp Gly Ala Arg His Ile Ala
            435             440             445

Ala Ile Asp Ala Phe Asp Asn Thr Gly Gly Ala Pro Val Ile Val Met
        450             455             460

His Leu Gly Asp Gln Asn Asn Ala Trp Ser Phe Tyr Lys Asp Asn Ile
465             470             475             480

Tyr Arg Gly Tyr Asn Gly Gly Tyr Val Trp Gly Ser Trp Asn Phe Asn
                485             490             495

Pro Ala Ser Lys Ala Asn Ala Asp Trp Ile Thr Asp Val Gly Ile Glu
            500             505             510
```

-continued

```
Gly Asn Asp Ile Arg Arg Pro Tyr Val Arg Arg Ala Ser Asp Gly Tyr
    515                 520                 525

Ile Val Arg Met Pro Arg Asn Phe Ser Gly Asn Ala Leu Glu Val Gly
    530                 535                 540

Trp Asp Gly Gly Leu Arg Trp Tyr Val Asp Gly Val His Gln Gly Ala
545                 550                 555                 560

Met Val Ser Asp Thr Asn Trp Arg Gly Ala Phe His Asn Asp Ala Gly
                565                 570                 575

Arg Ile Gly Arg Gly Gly Asp Trp Ser Ile Gly Asn Gly Tyr Phe Asp
                580                 585                 590

Val Val Ile Asp Gly Val Ser Tyr Gly Val Pro Phe Asn Pro Ser Asp
                595                 600                 605

Ala Arg Arg Lys Glu Asn Ile Val Pro Ser Thr Glu Asp Ala Ile Glu
    610                 615                 620

Lys Val Lys Gln Ile Lys Phe Tyr Ser Phe Asn Phe Lys Ala Asp Gly
625                 630                 635                 640

Leu Met Asp Ser Lys Lys Val His Gln Thr Gly Phe Ile Ala Gln Gln
                645                 650                 655

Leu Gln Gly Val Asp Pro Ala Leu Val Ile Gly Asp Asp Asn Pro Asp
                660                 665                 670

Met Thr Leu Ser Pro Asp Val Asn Ser Leu Leu Ser Leu Ala Leu Lys
                675                 680                 685

Ser Ile Gln Gln Leu Asp Ala Lys Ile Ala Val Leu Glu Glu Thr Ile
    690                 695                 700

Leu Ala Leu Lys Gly Asn Pro
705                 710
```

```
<210> SEQ ID NO 3
<211> LENGTH: 39455
<212> TYPE: DNA
<213> ORGANISM: Unknown
<220> FEATURE:
<221> NAME/KEY: MISC_FEATURE
<223> OTHER INFORMATION: Bacteriophage RKP181 host recognition domain
      containing C-terminus of the tail fiber protein
<220> FEATURE:
<221> NAME/KEY: DTR
<222> LOCATION: (1)..(239)
<220> FEATURE:
<221> NAME/KEY: ORF1
<222> LOCATION: (404)..(634)
<223> OTHER INFORMATION: encodes hypothetical protein
<220> FEATURE:
<221> NAME/KEY: ORF2
<222> LOCATION: (1304)..(1504)
<223> OTHER INFORMATION: encodes hypothetical protein
<220> FEATURE:
<221> NAME/KEY: ORF3
<222> LOCATION: (1769)..(2011)
<223> OTHER INFORMATION: encodes hypothetical protein
<220> FEATURE:
<221> NAME/KEY: ORF4
<222> LOCATION: (2022)..(2441)
<223> OTHER INFORMATION: encodes hypothetical protein
<220> FEATURE:
<221> NAME/KEY: ORF5
<222> LOCATION: (2519)..(2764)
<223> OTHER INFORMATION: encodes hypothetical protein
<220> FEATURE:
<221> NAME/KEY: ORF6
<222> LOCATION: (2820)..(3002)
<223> OTHER INFORMATION: encodes hypothetical protein
<220> FEATURE:
<221> NAME/KEY: ORF7
<222> LOCATION: (2999)..(3178)
<223> OTHER INFORMATION: encodes hypothetical protein
```

-continued

```
<220> FEATURE:
<221> NAME/KEY: ORF8
<222> LOCATION: (3175)..(3495)
<223> OTHER INFORMATION: encodes hypothetical protein
<220> FEATURE:
<221> NAME/KEY: ORF9
<222> LOCATION: (3492)..(3857)
<223> OTHER INFORMATION: encodes hypothetical protein
<220> FEATURE:
<221> NAME/KEY: ORF10
<222> LOCATION: (3870)..(4049)
<223> OTHER INFORMATION: encodes hypothetical protein
<220> FEATURE:
<221> NAME/KEY: ORF11
<222> LOCATION: encodes hypothetical protein
<220> FEATURE:
<221> NAME/KEY: ORF12
<222> LOCATION: (4320)..(4586)
<223> OTHER INFORMATION: encodes hypothetical protein
<220> FEATURE:
<221> NAME/KEY: ORF13
<222> LOCATION: (4651)..(5007)
<223> OTHER INFORMATION: encodes hypothetical protein
<220> FEATURE:
<221> NAME/KEY: ORF14
<222> LOCATION: (5058)..(5465)
<223> OTHER INFORMATION: encodes hypothetical protein
<220> FEATURE:
<221> NAME/KEY: ORF15
<222> LOCATION: (5469)..(5570)
<223> OTHER INFORMATION: encodes hypothetical protein
<220> FEATURE:
<221> NAME/KEY: ORF16
<222> LOCATION: (5567)..(6499)
<223> OTHER INFORMATION: encodes ATP-dependent DNA ligase
<220> FEATURE:
<221> NAME/KEY: ORF17
<222> LOCATION: (6496)..(6615)
<223> OTHER INFORMATION: encodes M56 family metallopeptidase
<220> FEATURE:
<221> NAME/KEY: ORF18
<222> LOCATION: (6768)..(9365)
<223> OTHER INFORMATION: encodes DNA-directed RNA polymerase
<220> FEATURE:
<221> NAME/KEY: ORF19
<222> LOCATION: (9385)..(9831)
<223> OTHER INFORMATION: encodes hypothetical protein
<220> FEATURE:
<221> NAME/KEY: ORF20
<222> LOCATION: (10012)..(10257)
<223> OTHER INFORMATION: encodes hypothetical protein
<220> FEATURE:
<221> NAME/KEY: ORF21
<222> LOCATION: (10254)..(10553)
<223> OTHER INFORMATION: encodes hypothetical protein
<220> FEATURE:
<221> NAME/KEY: ORF22
<222> LOCATION: (10616)..(10921)
<223> OTHER INFORMATION: encodes hypothetical protein
<220> FEATURE:
<221> NAME/KEY: ORF23
<222> LOCATION: (10914)..(11609)
<223> OTHER INFORMATION: encodes hypothetical protein
<220> FEATURE:
<221> NAME/KEY: ORF24
<222> LOCATION: (11590)..(11763)
<223> OTHER INFORMATION: encodes hypothetical protein
<220> FEATURE:
<221> NAME/KEY: ORF25
<222> LOCATION: (11831)..(12496)
<223> OTHER INFORMATION: encodes Putative ssDNA binding protein
<220> FEATURE:
<221> NAME/KEY: ORF26
<222> LOCATION: (12499)..(12966)
<223> OTHER INFORMATION: encodes T7-like phage endonuclease
<220> FEATURE:
<221> NAME/KEY: ORF27
<222> LOCATION: (12968)..(13438)
<223> OTHER INFORMATION: encodes lysozyme [Peptidoglycan recognition
```

```
       proteins]
<220> FEATURE:
<221> NAME/KEY: ORF28
<222> LOCATION: (13545)..(15230)
<223> OTHER INFORMATION: encodes DNA primase/helicase-like protein
<220> FEATURE:
<221> NAME/KEY: ORF29
<222> LOCATION: (15240)..(17348)
<223> OTHER INFORMATION: encodes DNA polymerase
<220> FEATURE:
<221> NAME/KEY: ORF30
<222> LOCATION: (17398)..(17775)
<223> OTHER INFORMATION: encodes hypothetical protein
<220> FEATURE:
<221> NAME/KEY: ORF31
<222> LOCATION: (17798)..(17998)
<223> OTHER INFORMATION: encodes HNS binding protein
<220> FEATURE:
<221> NAME/KEY: ORF32
<222> LOCATION: (17995)..(18879)
<223> OTHER INFORMATION: encodes phage exonuclease
<220> FEATURE:
<221> NAME/KEY: ORF33
<222> LOCATION: (18901)..(19212)
<223> OTHER INFORMATION: encodes hypothetical protein
<220> FEATURE:
<221> NAME/KEY: ORF34
<222> LOCATION: (19226)..(19591)
<223> OTHER INFORMATION: encodes hypothetical protein
<220> FEATURE:
<221> NAME/KEY: ORF35
<222> LOCATION: (19594)..(19896)
<223> OTHER INFORMATION: encodeshypothetical protein
<220> FEATURE:
<221> NAME/KEY: ORF36
<222> LOCATION: (19901)..(21496)
<223> OTHER INFORMATION: encodes Putative head to tail joining protein
       (collar)
<220> FEATURE:
<221> NAME/KEY: ORF37
<222> LOCATION: (21557)..(22381)
<223> OTHER INFORMATION: encodes Putative capsid assembly protein
<220> FEATURE:
<221> NAME/KEY: ORF38
<222> LOCATION: encodes Putative major capsid protein
<220> FEATURE:
<221> NAME/KEY: ORF39
<222> LOCATION: (23560)..(24138)
<223> OTHER INFORMATION: encodes Putative tail tubular protein A
<220> FEATURE:
<221> NAME/KEY: ORF40
<222> LOCATION: (24141)..(26507)
<223> OTHER INFORMATION: encodes Putative tail tubular protein B
<220> FEATURE:
<221> NAME/KEY: ORF41
<222> LOCATION: (26615)..(27079)
<223> OTHER INFORMATION: encodes Putative internal virion protein A
<220> FEATURE:
<221> NAME/KEY: ORF42
<222> LOCATION: encodesPutative internal virion protein B
<220> FEATURE:
<221> NAME/KEY: ORF43
<222> LOCATION: (27663)..(29846)
<223> OTHER INFORMATION: encodes Putative internal virion protein C
<220> FEATURE:
<221> NAME/KEY: ORF44
<222> LOCATION: (29865)..(33749)
<223> OTHER INFORMATION: encodes Putative internal virion protein D
<220> FEATURE:
<221> NAME/KEY: ORF45
<222> LOCATION: (33833)..(35968)
<223> OTHER INFORMATION: encodes putative phage tail fiber protein
<220> FEATURE:
<221> NAME/KEY: ORF46
<222> LOCATION: (35968)..(36294)
<223> OTHER INFORMATION: encodes Putative uncharacterized protein
<220> FEATURE:
<221> NAME/KEY: ORF47
<222> LOCATION: (36294)..(36506)
```

-continued

```
<223> OTHER INFORMATION: encodes Putative lysis protein
<220> FEATURE:
<221> NAME/KEY: ORF48
<222> LOCATION: (36503)..(36775)
<223> OTHER INFORMATION: encodes Putative packaging maturation protein A
<220> FEATURE:
<221> NAME/KEY: ORF49
<222> LOCATION: (36798)..(38579)
<223> OTHER INFORMATION: encodes Putative packaging maturation protein B
<220> FEATURE:
<221> NAME/KEY: ORF50
<222> LOCATION: (38795)..(39007)
<223> OTHER INFORMATION: encodes hypothetical protein
<220> FEATURE:
<221> NAME/KEY: DTR
<222> LOCATION: (39217)..(39455)

<400> SEQUENCE: 3
tctcatagaa tgagccgctg ggattacccc catagggggt ccacttgggc cactggggca      60
ggcaggaggc ccccccgggt gccctctcg gcactccctg aggggaaccg gcagggtcaa      120
cccactggat ttaacataat ggaccttatg cgcaatccct ataggtcaca ttgagggtac      180
tgataggggc tctctatggg ctcctctggg gtgataggag ggctctatgg gtttccctat      240
ctgtaggacc ctgaggggca ccctgctatg ccctaccctg aggggcgccc ctttgggaca      300
cctgctaggg accgtgctgt atcccttgcc ttacctgcta tgggctctat actacagggt      360
gaccctgagg gtgtcaatcc ctgagggtca cattccggga gacctacatt ccaaccagtg      420
cggccctaat gcttgtcttc gtgtagaccg caccgtctgg cgtcttggtc atcccgtatg      480
cttgcagcat ctcaaacagt cgggcggcgg cttggtcctt ggtccggtaa gccttcaggc      540 attgctcgc ctgtctatat agtccttcgt cgttattgat ccagagggag acattccact      600
gttgccagtt cttatgccca ttgtatccag ccatgatgca ctccttgagg gttacacatg      660 aggggacta caggacccat gataggggct atctgtcatt gcgtcaatag ggtaaaccct      720
tgggcgagtg tatttcttgt ctcagtgggc gacaatttcc cgtgcctcta tatagggcga      780
gagtcagccc attaacacac actaaagaaa gtgcatgttg cctattgacg gcctaccgat      840
tctcaggcaa gattcgtctc acggtgttgc aacgcagcgc cggaccggga gaccgggacg      900
atctttaaga atctgaccaa atgactgttg acagacacgg ttacatgctg atacagtgtg      960
taccagtcgc aacgcagtag cccctgagag tcaaagccga cgttaaatgc tagggttgaa      1020
cagtatgtgt ccctcctttc cttgattggg cgagtgatac gcgacaacgt gttagatgca      1080
gcctaggaca gattcctgag aatgcaagta gagattgaca aagcgcagcg aatactgcac      1140
aatgcggtct cagtagtaac ggaacagcag caacgttccg gcagtaacag aaagtgattg      1200
acaaggtgaa gcgaagtatg cgacactgta gtccaaggta gcacaagacg caacactccg      1260
caagggtgtt gtgatgatcg aacgaagaca acggaacgca cacatgaacc cgatcaagcg      1320
cgcactgcac cagtaccgcg aagcggccaa gatggtcctc gccaagcact tcggttacat      1380
tgtgtggtcg gctgagtacc gcgcaataca cgtctccttc accctcaagg gtgccatcga      1440
gtggcaagcc tgctacgacg atgcggtgat cgtggcggcc cagcgagtgg tccgtttcgc      1500
ctgataccgg caagggtatc ggttgacagt gtagggcgcc accaatcgca gcacggcgca      1560
tgggcaacgg cccagtagga aacccgcata gcgacgggta ggaccctgc aaggggaacc      1620 acggggcgac cggctggggc gtccgatgga ataccagcac acaattcggg ttgcgtaggg      1680
ggctcagagt gtcccaatgc gtagtggata cggtgacgat tcatcctctg tcctagtgaa      1740
acgagctaac gtgtaagacg cgaaccgaat ggctaaatcc gaagggctga cccgcaaggg      1800
```

-continued

```
tcggtccttc cagtgtaggc attcccgccc aaaccgcaag gactttttca tgtactacct   1860
catcgagtat gacgatctgt gcaaggtgga tcacgcaagc tgggtcgtca agcgatacga   1920
ggagtacgcg gacatacccct ccgcgctcga ccgctgtggc gaactgatca tgcaaggcca   1980
tgccgtacac atccaacccc tcacccgcta aggactcaac catgagcaac ccctttgtca   2040
tcatgtccgc attccgtcaa gggctctccc aagaggagaa cctcaagcgt caccactcgc   2100
tggacgccac tgtgggcacc atcgtggggc aacaccctaa gctgaccctc ggctcctatg   2160
tggaggagga aacgcaacgc ccgggcatcg agttgggcgt gcgcatcgag ccaacagcac   2220
aaaccagctt tgcaaaggta gtgcaagtcg ctctccggct tgccgagcac ttcgagcaag   2280
attcgattct cgttgtcgat cacggcgggc aagcaacgct tgtgtaccgt gacggacgcg   2340
ccgatgaagg agtcggaaat tggacgaagg tgtctcaagc tgaggcattg cggtctccgt   2400
actggaccaa catctcggga tcgtactaca aggccgtcta agttgcaacg cccaagggca   2460
tccgatcagg gtgtccttca acgtttcaac cgcaaacttt ccgcaaggat accacgccat   2520
gagcgaacaa acaatacgca tcaacgttgc gaagaagcaa ccacagcccg ggttcggcgg   2580
caagcctgtc taccgccacc actgcgccgt ccacctcgac tggctctccg atctggacaa   2640
ggtacatgag gtagtgcagc aactccgcgt ggccttcccg gtgggcgagt accacatcac   2700
ggtcacccgc tgggtcctcc gtggggaaca catcaaggtc gaaggctgtg acgacgaccg   2760
ctgaggtcct gcaagggtgg ctagtgtggc gcgatcaggg atcgtccggt gggtggaccg   2820
tgggggtcta cctgtgggaa cccgatgcgc tgcgctacat ccgggagaac cggggcgaac   2880
gcctcaaggg ctggtggccc acgacctact cccgcaccta ccgccaccgc gctgtgcagt   2940
gtgtccgcat cgacgggacc ctgcatgtcc tccaaccctg tcacgagaac ccgccgatat   3000
gagcgcaagt caaggccaac tggtcgaggt ggttgtcacc ctgaagggca accgccaaga   3060
gacctacttc atcaccggat tgccgaacgc aaggggcgta tcccgcctgt tcatgggcaa   3120
cccgcaagtc ctgaaagttg aactgctgta caccggagaa cgaggagcaa cccgatgatc   3180
gtcaacgctg caaccttccg cgccatcctg cgcaacatcc ctgccaacgc gctgcgcccc   3240
atcatcgagg gcgatctgtc gcgtgtcgag gtcaaggaca ccacatggct ccatgcgccc   3300
atcttgggga ccttctcggg caccaaggac ggcaacgtgg tggtcaagtt ctggggcgac   3360
gattacccgc tcctgtactc gctggcaacc gagctttaca acaaggccgg ggacatcacc   3420
atcgtgcaag ccctcgcgtg gatcgcgttc cggtcctacg aggaagcgtt cgcaaccagc   3480
aaggaggcag catgagcgaa gccgtccagt acctcggcca cggcccggag ggtggcattc   3540
aggaacactc caagggcaag ctgcatccct tggtctgcgt ggtcaaggaa ccgcccgccg   3600
atctgatcga ccagcgcaag ctgacctact ggatcgaccc cgcgcaagggc ggcaaggacg   3660 ttaccggcga atggcgcgat ccgttcttcg ccctgaagta cgcaatcctg tattcgtggg   3720
gatacaagtt cgacaccgag cgcccgctgg gcgtgggtct ggaactgttc gccgctgccg   3780
agggccgcac cgtggattcc ctgtaccgcg aggcccagaa catctccgcc gccgagcatg   3840
gccgtggatt cgtctaagga ggaggacgca tgaaccgcat ggaccgcaca agcctgtccc   3900
gcttatgtct cgtgctgttg ctgtgcgtgc tgatcctggc cctgctcggg ctgggcggct   3960
gcgcagtcaa caccgtgacc atcaacaacc acatcgaggt gcatgacagc gccatcgacg   4020
tgcaagccaa ccgcctcacc cgcatctaac ccgcaacctc aaggagatac caacatgctg   4080
cgttccttca atgccttcat cgcccgccgc tggaacaact tcaccacggc tgtggcgttc   4140
gtgatcaacc tgccgatcat cttccacatc ctcgtggtgc tggtcgcgct gctgatcgga   4200
```

```
atcggggccg tggtctggtc cgtggtcgag tcgggctggc tggtgatcaa ggccctcgcc   4260
accctcctgt gggcgccctt caaggccatc ttcgtggtcg gtgcggtggt ggccgatggg   4320
tggaccagcg cggggttctg agcgtggccc tgtcaaccgt ccgcgctgtc aagttctggc   4380
ggcgcaacca cgaggggacc ctcaaggcgt cccactggca gtacggcttg ggtccctgcg   4440
gcgagcatgt ggggaccctg cgtgctggct tcgacggtga ctggctggtg atccaccagt   4500
acaccgacaa gaccgagaag ctgttccatt tccatgtccg tgacatcgcg ggcaaggtcg   4560
agttcctgct gttcgaggag ccgtgaaatc aggggggcatc ctcaagggtg cctccgagtt   4620
tcatcccaac cactcaaagg agagtgaacc atgcgtcaat ccgccatcga caccagcctc   4680
gcccccgaac tgaacgcccg caacgaggcg agcagcacgt acccgttcga ggtcgcctat   4740
gtgggcgagt actggcgagt gcaggacaac cgcaccgggg gcctgtcttc gacccgccac   4800
cagctttaca agagcgccga ggacgaagcc cgcgaactga aggccaagca gcaggccgac   4860
aacgcggcca aggttctggc ccaagccgag gcaagccccg ctccggtcgc tgagcccgag   4920
gcaacgcaac ctgccgctga accggccaag ccgacccgcc gccgcaaggc gaaggccgag   4980
gcgattgtcg ccgccgaact gaagtaagcc acccgctcaa tcctggccct acgggggcca   5040
ccctttaagg aaccctgatg attctccgca acgctcccgc cctcggcttc acctttgctg   5100
aggcccgcgc cgctcgcctg ttgtctgcct cctcgcctga agcgtgggcc gcaacccagc   5160
agcgcaacgc catgatccac acggccaccg atccggtcct ccgcgcacaa gccgacgaga   5220
aggcgcgcaa ggccctccgg gactccctca agaaagcgat ggggatggcc gcaacggggc   5280
atggcccggt gggcgtgttc aagcgggggga ccatccgggt gtcccgcgag ggtgtctccg   5340
tgggcatccc tgcgcatctg gtcgaggagg tctcgcccga gttccgcgag gaggtggccg   5400
atgctgtgcc cctcaacgcc accgcgagca acacccgcca ccacaacccg aagcgcaagg   5460
actgagccat gagccacgac aaccaaggat tcgagaagtc ccgcaacacc aagccccgcc   5520
gcgactgggc ggacctgcaa gctgcccgca agcgcaagga gaagcgatga gccaagccca   5580
ctacctgacc aacggttacc acgagttcaa gccacggggc gctgtcccgt tcgaccgcaa   5640
gggcatcgcc gctgccatcg agcgcactgg ctatgtccac atggcctaca aggtggacgg   5700
cgtgcgggtc atcctgcaag tccacccgga tggccgcgtg acctgcacca gccgcacgag   5760
caaggtcctg cccgcgctgc gcctgctggg cgccgaccct gacctccggg agaggctgcg   5820
cgagaagtac ccgcgaggcg tggtgctgga ctgcgaaatc tcagtcgtgg gccggtcctt   5880
tcaagagggc tgtggcgacc tgcgccgcaa ggtgccgatt gacccgacct cgctggtggt   5940
ctggccgatc ctccagtacg cctacgacga ggtggtcacg ggtgtctacg ccccggtgac   6000
gctgggtgtg cgcatggcct acgccctgac gctggccgag gaactgtcgc cgctgctggg   6060
cttcttggtc catgacctgc gcatcgggaa catcaccagc gtggacgaca tcgagcccca   6120
gttcgaggtg gcccgcgcc tgagttacga ggggctgatc gcctacgacc cggccaacga   6180
tgtcttcgac gggggcaagc gcgtgggctg gtggaaggtc aagcccgagt cggacatcga   6240
cggcaaggtg gtgaactgga tcgagggcac cggcaagtac gtgggcatga tgggcgccct   6300
cacggtcgag tgcgaggacg ggaccatcac ggacgtgggg accgggttca ccgacgatca   6360
acgcaagctg ggccgcgagt actggcttgg ccgtctggtg caactgacgt tcatggaacg   6420
caccgacgat ggcaacctgc gccaccccgc cttcgaccgg atgcgcgacc tcgactccgc   6480
accggggctg aagtcatgat cgactggccc ctcgtggggc tcctcgtgct ggccgcgctg   6540
```

-continued

```
gtcctcgtgg gcgtctgcct gacctacctc gggcggctca ttgaggagga ggtctcggac   6600
cccttcaacg attaacccac actagagcac agtgtcgaat cccttaggtg cgattaaccc   6660
gcactatagg gggttcctct ctgttctcct gaaagataaa ccttaaaggt ccctgagagg   6720
ggttcctgac aaggtagaca taaacaagat taccctatag gaaccctatg agcgatgctt   6780
tgcaaaccct gaccagcctg tacggtgctg atctggctga ggcgcaacgg gccatcgagg   6840
cggaagccta cgagattggt gcccaacgtt tcctcgctgc gatgcaggcc aaggccgagc   6900
ggggcgaggg ggcggatacc aaggtggccc gcccgctgat tgccgacttg atccccaagg   6960
tggaggcagc aatcaacgcc ttcatcgagg tcgcattctc cggcaaggct ggcaagaagc   7020
ataccgccgc caagctgatg gcgaaggtca actccaaccg cgtggcgttc atcgccctgc   7080
gtgtcgtgct gaactccctg tcgcaagtga gcggcgggtc gggtggcaag aagcccgcaa   7140
ccctcgttgc tgtgtcgatg cagatcggcc atgacattga ggacgaggcc cgcttcggac   7200
gcatccgcga cgacaacgag aagcggtaca aggacaatat tgcggtgaac atcgccaagc   7260
gttccggcga ccacttcaag cgagcctatg ctcgcgctgt cgaggttgcg atggaggacg   7320
cgggcgagtt gcaggagtgg gatggctggt cgaaccaaga ccgcgccgct gtggggctga   7380
agctggtcga gttgatcatt gaatcgactg gctggtagaa actgcgccac gagcacaagg   7440
gcaatccaaa gttgcaccga gtagtgctgg aaatcacgga cgcatacgcg gagtggctgt   7500
ccaagcggac gcactccctc gcggacatga cccccggcatt cgccccgtgc gtggtccctc   7560
ccaagccttg ggtcgggaac cgtggcggtg gctactggtt caacgaggac aagtctccac   7620
tcatgctggt gcgcgggtct gtccgccgca accgccgcta caaggacgtg gacctctcaa   7680
acgtgctggc cgcgctgaac gcgatccaga ataccccgtg gacgatcaac gccaaggtcc   7740
tggccgtggc cgaggaggtg gcgaagtggc ccaaccctcc ggtcaagaag atgccctccc   7800
acgtcacgct gcaaaagcct gaacggctgg aaggcatgga cgaggacgag gaggtcctgc   7860
gcaagtggaa gaaggacgcc gcgctggcct accgcaagga gaaggcccgc cgctcgcgcc   7920
gctaccaact ggagacctca ctggtgcaag cccgcaagta cgccgggttc gagcgtatct   7980 ggttcccta ctctctggac ttccggggcc gaatctacgc cgcgactaag ttctccccgc   8040
aagggcagga cttggacaag gcgctgctgc tgttcgcgga ccctcccgag attggcgagg   8100
acggggcgtt ctggctgcgt atgcacctcg ccaacaccgc aggcttcgac aaggagacct   8160
tggacgaccg aatcaagtgg acgcacgaca acgagcaact gattctggag accgccgcca   8220
acccactcga caatctctgg tgggccacgg atgcggactc gcccttctgc ttcttggccg   8280
cgtgcttcga gtacgcagcg tggaaggagc aaggccccag ctatcgttgc ggtctggcga   8340
tagcgttcga cgggtcctgc tcgggcatcc agcacttcag cgcgatgctc aaggacgagg   8400
tgggcggcaa ggccgtgaac ctgatcccct cggagaaacc ctccgacatc taccgcatcg   8460
tgtccgacaa ggtgaacatc gtgttgaaac gcgatgctgc cgatgggtct gacgactaca   8520
cggacaccaa ggtggatgac gacaccgggg aaatcaccga gaggccccga aggggaccc   8580 gctcgctggc ccgccactgg ctgaactacg gggtgaaccg caaggtcacc aagcggtcgg   8640
tcatgacatt gccctacggc tccaagaagt acggattcac ggaccaactg ttcgaggaca   8700
tcgtgcaacc cgcaatcgag gagatgggcg aggacgtgtt cccggccccg ggcgaagcct   8760
gctcctacat ggcggggcctg atctgggacg cgctgggcac cacggtggtg gccgctgtcg   8820
aggctatggc atggctccag aaggtggccg ctgtgctggt tgccgagcag atgccgtgcc   8880
actgggtcac gcccgctggc ttcccggtct ggcaggagta ccgcaagtcg gacacgcatc   8940
```

```
ggatcgacac catgatctgt gggaacatcc gcgtgaccat gaccgtcaac aagtccgagg   9000
cgcagaccgg cccgaagccg ctggaccgct acaagcagca gaacggcatc tcgcccaact   9060
tcgtgcatag catggacgca agccacatga tgctgacctg cctgtcggcc agtcgccaag   9120
gcatcgagca cttcgccacg atccacgact cgttcggcac cgcacccggc cacgctggcg   9180
tgatgttccg gacggtgcgt gaggtcatgg tcgagaccta cacctcgcag gacgtgatcc   9240
agaacttcta cacgaccttc gactcgctgc tgtccccgga cgcacgagac aagattccgg   9300
ctttcccgga gaaggggtcc ctcaacctga tggacatcct caactcgcag tactgcttcg   9360
cttaactctc aaggagaaca ccacatgcaa tcgaccatcg cccaagccca cgccctgaac   9420
accccggaag ccaacctgat gcaccgcatg gcccacattc agcgcatgga ggaactggtc   9480
catagcatca ccgaggaggg cacccaagcc cgcgtcgatc tggaagccca catcgacaac   9540
ctccgcacgg aaatccacgc agtctaccgc gccgagaagc acgaccagat tcgtgcccgc   9600
catgcgtatg cccgcaaggc cacggtcgag gcgctgcccg ccgaaggccc ggtctaccaa   9660
gcgggtcccc tgtcggacac cttcgtggtc tcctccggcg aacgcaccga ggtcggcgtg   9720
ctggtcccgg tcctgcactc gcccatcgac ggcgaaccgc tggtcccggc tggcctgctg   9780
gcccgcgcat gggccgctgt gaagggcgtg ttccaccgtg ccgcgcacta acccttcgag   9840
gatcacccac gcgggcacca cgctggtcct tgtctatacc gacgacgagg atcaagcgtg   9900
cgcccagtgc gcgttgacca agctgaagaa ctgctccgcg atcccgggcg ccgcaaggtg   9960
tgcccacaag gatcacggct tctggattcc cctcaaggag ataccccgac tatgaacaag  10020
aagcaagccc ctgaacacaa ggacgtgacc ggcaaggtca tcaagctggg cgataccgtg  10080
gcgttcgcca aggctgggca ctgcgcgctg tacgtgggcc agatcacgaa gattcacccg  10140
aagctggtgc gcgtggcctg cacgacccgg cacaagcact acatgagcgg cgcggttgtc  10200
gagcagacga acgagtacga ccgccacccg ctggacaccg tagtggtggc agcatgaccg  10260
tgggccgaca ctgcaccaac tgcaagcatc acatcgacgg ctactggaat caggagtgcc  10320
gcaagttctc caaggaggag acccgctggg aacccgtgca gggtccctac aagtaccgca  10380
acgctgtgac ctgcgacgac gcccgctcgc tgaacggcct gtgtggtgtg caggggaaat  10440
ccttcgaggc atcccgctgg gcgaccctca aggataagtt ccgctgggtc tacctgctgg  10500
cgcccgtggc gggtctcatc gtggggcaca tcctggcccg agtgttcgcc tgattaaccc  10560
acactagagg acaccccacg gcaccccgct gtgggacctc aaaggagata cgactatgac  10620
gcttgagctt cgccgccgca acaacggcca aagcgtggtg ctggttcccg actcgcgcag  10680
catcgactgc gaacggaacc gcaacggcaa ccgcaaggcc atcgcaacgt tcaccccgcc  10740
gtacacccgc tcccgtgtcg agaagtacat gggcaaggtg gtgctggtct ccccggcact  10800
gctgcaacag gccctcgctg aaaagcgtgt ggcactggac cacgatccgc gccgcttcct  10860
gaaggcccgc gctgccctgt cgaacgcatg ggctcgcgtc aaggaggtgt ccgtggatg  10920 acgcaacacg ccaacgcgct ctggaatccg tgaagggtct cggcctcgcc gctgaccatc  10980
cgggcgcggg caaggacacc gccttcgcat cgctgcaagc cgccaacccg gggaccgatt  11040
tcgtgaacgt caagttcgcg gatgccctga ccgccgaggt gcgcgcactg ttcccgaagg  11100
ttacggacga cgagttcacc gagattcgca acgacccgaa gttcaaggac ctgccgctgt  11160
ggatgtttgc gatccacaac atcgcccgca ccgagcaggg gctggactac gtggccttcc  11220
tgaagcacga gcaccccgaa ctgatccgcc agcgcatgtc gatccgtcag catctcctga  11280
```

-continued

```
tctacggcac cgagtacgtg cgtgagttca agggcgacga ggaccgctgg ctgaacctag  11340
gcgtggcgaa ggccaacgag gtcgccgcat cgggcaaggt cccggtgatc acggacgtgc  11400
gcttcgtgaa cgaggccatc aagctgaagc aggccggtta cgacatcgcg cacatcgctg  11460
ccgatggtct ggcgaacgcc gccctgtccg ccctgaccgg cattgccgag gggcacctga  11520
aagactggga ctttgacctc cgcgtgaaga acgtgtgggg caagcccgag aacatgggag  11580
tgcaattcaa tgccaagtac cgctggtaag gcactgaagg tttccgtgt gcggtacgcc  11640 ctcgaaggga ccccttacgc caccgctgtg gaagtcaagg cggtctccat cgacgctgcc  11700
tatgaggccg ccgaggagat gtaccccaac tgggaaatcg aagcagtgat ccaagtggga  11760
taacccacac taaaggacaa catcaaggga ccctccgggg tcctttctca tttcagaagg  11820
agaatcacac atgagcaacg cacccgcaca agccgacaag ccgaccacgc tggtgacccc  11880
gctggcgacc gtcttcggct tcgtcaacgt caccaagccg gacaccaagt acaagcccga  11940
gggcgagtac aagattcgcg tgaaggtccc caaggaggcc gcgcaggacc tctacgagaa  12000
gctggccgct caagccgagc gcaagctgga ggagaccatc gcccgcgcca agaaggacgc  12060
caagttcaag gccagcctga agggcaaggc accgaaggcc gctgacctcc cgttctacga  12120
ggacgaggaa gacggcacct acgtgttcac cttcaagagc aaggccagct cgtcagcaa  12180 gaagccgggt tcggaaggcg agaccatcaa ccgcacggtc ccgatctggc aaggcaacaa  12240
gcgcctgaag ccgaggagg tgcccaagtt tggcgagggc tcgcaagtcc gcgtgtcgtt  12300
cgtggccgct gacttcttca ccgctgccgt gggcgctggc atcacgctgc gtctggaggc  12360
cgtgaagctg atcaaggcag tcgagtacac cggcggtggc agcaacccgt tcggtgacga  12420
agatgaaggc gactaccaag agtccaccgg caacgagttc ggtgatgacg aaggtggcgt  12480
ggacaccgag ttctgatcat ggcaggccgt ccgttcaaac gagcgggcgg ctggggttcc  12540
cataacccat cgacctatcg cagcggtctg gaggacaaga tcgccacgca actggagggg  12600
aagtcccttc cggttgtgtt cgagcagttc gaggtgaagt atgtaatccc agcctccgat  12660
cataaataca cgcccgactt cgtgctcccc aacgggatca tcatcgaggg caaggaatc  12720 ttcgacgcag acgaccgcaa gaagcatctc ctcatccgtg agcagcatcc ggacttggac  12780
attcgattcg tgttttcgag cagcaacgcg aagctataca aaggctcgcc tacttcctac  12840
gcgaagtggt gcgagaagta cggcttcaag tttgcggaca aactcattcc cgattcatgg  12900
ctccgagagc ccgggaccgg acgttcgctc gtttcactga cccgaaagaa aaagaaggag  12960
gcatgacatg ctccctaccc cgtacccccgg tctcccgccg atgaagaagc gggccacgac  13020
cgacctgatc gtcattcact cgcagacac caagcccacg atggattggg cgcacgcga  13080 cattcaccga gtccatgtgg tcgagaacca ctgggccgca atcggctacc acatcgtcat  13140
ccgccgagat ggcaccgtgg aaggtggccg accactcgac gctgtgggcg cgcacgctgc  13200
acaggtcaac tcccactctg tcggtgtctg cctcattggc ggctacgcg gtaaagccac  13260 ggacccgttc gagaagaact tcacgaaaga acaggccctg tccctccttg tcatcctcaa  13320
ggaactacgc gagaagtacc cgagcgcggc catcatcggc caccaagacg ttcagggttc  13380
cggcaagacc tgcccgaact tccccgcgaa ggcatgggcc gctgaacaca tccagtaggc  13440
cagcatcaag agaaacccc cgagggtccg taatgggctc ccgggggttt tttcgttcag  13500
ggccattaac ccacactagt ggaccaactc tgacggagat gatgatggca cgacaagaca  13560
atgaccgcga cgaatcatcg gacttcgttc gccacgtacc gtgcgacgaa tgcggcagca  13620
gcgatgcgaa ctcgctttac accgatgggc accagttctg cttcgcctgc gagacctacg  13680
```

```
taccgggtga tgggcaggaa ctcccagccg ggaagaaggg ccggagccag cgcgccgagg   13740
gcgtcctgag catgggcgag gccaacggcc agtacaaggc actgcaagcg cggggcatca   13800
ccgaggagac ctgccgcaag ttcggctact gggtcggcaa ggtgaagggc accccggtgc   13860
aggtcgctga ctaccgggac gtgaccggcg ctgtcgtcgg ccagaaactc cgagacccgg   13920
agaagaactt caactgcacg ggcaaggtcg cacgcggcca cctgtggggc tcccacttgt   13980
ggagcggcaa gggcaagatg atcgtgatca ctgagggcga gattgactgc ctctcggtgt   14040
cgcaactgca aggcaacaag tggccggtgg tctcgctccc cacggggggcc aaggcagcgg   14100 ccaagtcgtg cgccgagaac tacgagttct tggatggcta cgaccagatc atcctcatgt   14160
tcgacaacga cgagccgggg caggccgcga tggcggaagc tgctgaagtc ctcccggctg   14220
gcaaggtgtt tatcgccaag ctgccccctca aggacgccaa cgagtgccta ctcgcgggca   14280
agggccagga tgtcatcaac gcgatctgga acgcttcccc gtaccgtccc gatggggtgg   14340
tcgctgcgcg tgacctgatc gaccgcatca agacccgcgc cgtggtggag ggcatcaagt   14400 tcccccctcgg gcagaccctc aacgagatga cgctgggcat ccgcgagggc gaagtggtga   14460
tgctcacctc gggctccggg atgggcaagt cgtcgttcgc ccgtgagtgc gcctatgggt   14520
ggggccgcat gagtggcctc aaggtgggga tggcgttcat cgaggagtcg gtcgaggaga   14580
cctgccttga catcgctggc ttgcacctcg ggaagcgcat ccgccagttc cccgatgccg   14640
tgaccgtgga ggtccgggac tcggcgctga acgaactgtt caacaacgac acctatcacc   14700
tgtacgacca cttcggctcg gctggcgagg actcgctgct gaacaagctg cgcttcatga   14760
tcaccgtgct gggttgccag ttcatcatcc tcgatcacct ctccatcgtc gtgtctggca   14820
tggacgagtc cgaggacgaa cgcaagacca tcgaccgcct gatgaccaag ctgaagactc   14880
tcgccaagac aacgggcggg cgcttcgtgg tgatcagcca cctccggcgc aaggactcca   14940
agagcacgag tcacgaggag ggcgggcaga tcagcctgtc cgaactgcgc gggtccgggg   15000
ccatcgccca actgtcggac accgtgatcg gcttcgagcg cgaccagcaa ggcgaggacc   15060
cgaacctcgt caccatccgc atcctgaagt gccggttcac tggcgacacc ggggtggcgg   15120
gcttcctccg cttcaacaag gacaccgggc gactggtcga tgcgtggctc gaacagggca   15180
acgacttcgg gccggatgac ggcggctcca atcctgatga ccccttttaa ggagaaccaa   15240
tgattcaaga gaaattccca aaggtccgcc tgttcgacat cgaaacggac gggctgatgg   15300
agtactcggt gatcccgggg ctgacggaat cgtcggtggt gtccaaggtg cattgcatcg   15360
tgatccacga ctatcacgcc aactggtatc accgctaccg gtccgatgtg ccgggcgaca   15420
tcgagcgggc gctggacgtg ctcatggagt cggaccttct ggtggcccat aacgggatca   15480
agtacgacat ccccgtgttg gaactcctgt accgcacctt caagatcgac cgccgcaagg   15540
tgctcgatac gctggtcctg tcgaggctcc tgcacgccaa catcaaggac acagacaacg   15600
cgctgctgcg ccgtggggaa ctcccgggga aactctacgg gtcccactcg ctgaaggcgt   15660
ggggctaccg cgtgggcgag gccaagggtt cctacgggga aggcgagggc gatgtctggg   15720
ccgagttcaa cgaggagatg ctggagtact gcgagcagga cgtggtggtg acccgaaagg   15780
tgttcgaccg cctcctggca aactcctact acttcagcga ggacctgtcc tacacccagt   15840
acgcagtccg ccttgagcat gacgccgcgt gggtgctggc ccagcaggaa cggaacggct   15900 tcccccttcca cgagaagggc gccgctcgcg tctacgcgga actgtcaggc aagcggaacg   15960
acatcctgca acgggtgatg gagaccttcg ggtcatggta tgtggcgaag ggcggcaagg   16020
```

-continued

```
aagccttccg gcacccgcgc accggggcca agctgctgaa gtacccgaac gtgacctacc    16080
cgaagaccgg ggacatctac acgaagtccg gcaagctggc gaagatcgac tactgcaagg    16140
accggcccta cacgcctgtc gagcatgtgg tcttcaatcc gggctcgcgc cagcacatcg    16200
ccaaggtgtt gcaggagcgc ggctgggtgc ccgaggagtt caccgagacc gggcaaccga    16260
aggtggacga agaaacgctg gccgaagctg ccgagcgcct gcccgagcag taccgggagg    16320
acgtgaagct gatcgcggaa tacctgctgc tgatcaagcg gctgggccag atcgcggaag    16380
gcgacaacgc atggctgaag ctgtgcaatc gcgggtacat ccacggctcg gtcaacccga    16440
acggggcagt gaccgggcgg gccacccatg ccttcccgaa catcgcgcag gtcccctcgg    16500
ggactgccct ctatggcccc gagtgccgcg ccctctttgg ggtcgcctac gtgcgatccc    16560
gtccgggctg ggagaaggcg gtccaagtgg gcaccgatgc gtccggcctt gagcttcgct    16620
gtctggggca cttcatggcg aagttcgacg ggggccagta catcaaggac ctcctcgaag    16680
gcgatattca ctgggtcaat gtggagtcct tggggttcgt cccgaggggc accaagcgga    16740
tcaaggaagg ccccggccac gaggagcacg acaagttccg gggctacgcg aagaccttca    16800
tctatgcgtt cctgtatggc gctggtgacg agaagatcgg ctccatcatc ccgggcgggg    16860
acaaggcagt cggcaaggac ctcaagaaga aattcatgga gggcaccccg gccattgccg    16920
aactccgcgc actgctggag gagatgctgg tcgagcaaca gaagtgggtg gacggcgtgg    16980
cgcaggtcaa gtggaagcgc cgctggatca agggcctcga cgggcgcaag gttcacgtcc    17040
gctccccgca cgctgcgctc aacaccctgc tgcaatccgc tggcgccctg atctgcaagt    17100
actggatcgt ggagaccgag cggattctgg tcgaggagat gggcctgaag cacggctggg    17160
atggtggctt cgcctacctc gcatgggtcc acgacgagat gcagatcgcg gcccgcaccc    17220
cggagattgc cgagaagatc gcggaagcct cgcagaaggc catgcgcacc gctggtgact    17280
tcttcaactt ccgctgcctg ctggacacgg aatcgaaggt gggcgaccac tggggcgatt    17340
gccactgacc gattaaccca cactagtgga caacacattc tgaaaggagg ccaccacatg    17400
gcacgttcgt ttcaactcaa cgtttccacc cgcgtgaaag tggtggtccc cgattcggag    17460
atgccggaag tcgtgaaggc attcgaggaa ctgaaggtca tcgctgcgca actgcgcgtg    17520
ctggtcgagc gtgaggacat gccgaagctg cgctccatgt tcgcccgcaa cgaggacatc    17580
ccggatcgtg cggtcctgaa gatcgcccgg ggccgactgc gcgccttcgc caacatcggg    17640
gaggacctcg actcgttcat cctgttcagc gtcaagctga atctgaagga ccagttcaag    17700
gacaacctcg acggtgatgc cacgctgtcg ttcagcccgc ccaagttcga gaccgtcaag    17760
gtctacggcc agtaaaccat caacacagga gaattacatg aacgatctga tcaaagtctg    17820
caccgccatc caccaagacc cgaaggcgtt ccagtccgac tacgcccgca agcacgccta    17880
ccacatcgcg gaagctgcga gccgtggcct gatcacctgc atcacgatgg gcctgaaccg    17940
tggcaagtgg ttcgtgacgc aagagggcct gtccctcgtc aagacgcagc agcaatgagc    18000
gaacagcgcc tcggtctcct gatcgacgct gacttcctcg ctttccaagc agcggccaac    18060
gccacccgcg tggtcgagtg ggaagatggc gtcctgacaa cgtgggcgaa catggaggat    18120
tgcatcaacg ccttcatgac ctcgctggaa gcactgacct cgcgcaaccg ccgctggtcc    18180
accgcgaagg tgatcatgtg cttcaccgac gatcacaact ggcgcaagga catcctgccc    18240
agctacaagg ccaaccgctc cggcgtgggc aagggggaaac ccatcgccta ctggaagctg    18300
gtcgagtggg tccaccagaa cttcgagtgc ttcgtgcgcc cggggctgga gggcgacgac    18360
tgcatgggca tcctgtccac caagccgtcc ctcgtgggat gcacccacac ggtcatcgtt    18420
```

-continued

```
tccccgaca aggacttcaa gacggtcccc ggggagttct tctggatgac cacgggggaa   18480
aacctcgtgc tcaccgagga ggacgcgaac tactggcata tgtaccagac cctcatgggc   18540
gactcgacgg atggctacgc ggggtgtccc ggcgtgggtc ccacgagtgc cgctgagttc   18600
ctggccgagc cgtacatcgc gtatcaggcc acgaaggtcc tcaagtcggg tccccgaaag   18660
ggccaagagg agacctactg gaccacacga ccgctcgaag aaggcgagga cctgtgggac   18720
gggatcgtgt ccctgttcaa gaaggccggg ttgaccgagg aagacgcact ggtgcaggcc   18780
cgcgtggctc gcatcctccg cgcctcggac ttcgacttca aggccaagac cccgatcctc   18840
tgggagcgcc cgccgaagga ggatgtgggg accgaataac ccacactaaa ggagtcaagc   18900
atgtgcttct tcaaagcccc gaaggtggaa acgcccaagg tcgaaccaaa gccaaccatc   18960
accgagacct cggcacccga gccgcaggcc ctcgtggtgg gcggcgtgga cgacaaggcg   19020
gcatccgctg acggcgaatc caagtccagc aagaagggta cgggctcgct caagatcgac   19080
ttgtccccga ctgcttctga atcgggagat gccaatgtcg gaaccggcgc gaaccaagcc   19140
ttcaacgtca accgtggagg cggcggaccc gctcgcccca agaaggctgt cagtaagggt   19200
ccgacaatgt gacgacctcg ggttcatgag cgaggagcta gtgaaggccg cgtgggaagg   19260
ttccccgctg gcccagcgag cgttcctcga ttgggaatcc tactggcaac accagaagaa   19320
gttccacgag ggcacccagc aggcccagat cgttctcatg gacggcgaga cctgcgtggg   19380
cggcatcgtg ctgcacccct gtgaggacgc ccaagtaggc gaagccctgc tggcgctcca   19440
cacgttcatc cttccagcgt accgctcggt cgccaacctg aaggcccttc gagagaaggc   19500
ccggtgggtt gcgcaccagt gggacatccg ctggctggtc tttccacggg ggacccctga   19560
gggggttctc cacaagtatc tggaggttta actatgggtg gcatcaagaa ggcggtgacc   19620
aacatcatca agaagccgtt gcaggacgtt ggcatcatca agaacgaccc ggctcccgaa   19680
gcggccccgg caccggcccc tgctgcacaa ccggccccgg tgatcgcccc ggctcccccg   19740 ccccggctg ccgcaccggc tgcgcaagct gctgtgccga ccgatggcgg taacccggaa   19800
acccaagccg aggcgcaggc gaaggccaac cgtcgcggca agaagggcgt gaccatcaac   19860
cgcatctcgg gcggcggctc gggcctgaac gtctaaggcg atggcgaagc ccggtgaccg   19920
ctcgggcttg gacgaggaag cgcacgcgc gatctaccag cgactcatga atgatcgcgc   19980
tccctacgtg acccgtgcgg agaagaacgc gcagtacacc atcccgtccc tgttcccgaa   20040
ggcgagcgat aacgcctcaa ccgattaccc cacgccctac cagtctgtcg gtgcgcgtgg   20100
cctcaacaac ctcgccgcga agctggtcct ctcgaccgtg cccgtgggcg aacctttcca   20160
ccgcctcacc atctccgagt tcgacatcaa ggcgcaaggc gcccagactg gcgaggaggg   20220
ctctgtcatg gacaaggcgc aagtcggcct gtcgatggtc gagcgcatcg tgacggcgca   20280
cggcgaggca gcaggtttgc ggccaacggc cagcgaactg atgaagcaac tcctcgtggc   20340
cggtaacggc atgttgcact tgcccccggg agaggtggca accaagctgt accgcctgtc   20400
gtcctacgtc tgcgagcgtg atgcagtggg caacgtcctg caaaccatcg cgctggacaa   20460
gctggcgtat gtggcgctgc ccgaggacct gaaaggctcc ctgccccagc aggactacga   20520
gcccaaccaa ctgatcgaga tttacaccca ctgctaccgc gacctcgaaa gcgatggctg   20580
gctcgaatat caggaggtcg agggcgaagt ggtgaagggc tccgagaaca cctacccgaa   20640
ggaagcctcc ccgtggattc ccatccggct ctacaagctg gacggcgaga actacggcga   20700
ctcgttcgtg gaggagtaca tcggtgacct cgtttcgctg gagaacatct cgaagtccat   20760
```

```
cgtgcagttc gccattgcgt gctccaagat tctgttcctc gtcaagccgg ggtccagcac   20820
ttcggtgcgc cgtgtggcga aggccaactc gggcgacttc gttccgggca agaaggagga   20880
catcgaggtc ttccagatgg agaagttcgc tgacttccag atcgtggaga aggtgggcaa   20940
caacatagag cagcgcctgt cgttcgcgtt cctgctgaat agcgcggtgc aacgctcggg   21000
cgaccgggtg acggctgagg agattcggta cgtgtcgcag gaattggagg ccacgctcgg   21060
cggggtctac tcagtactgg cgaccgaatt ccaactgccg ctggtccgcc gctggctggt   21120
tgacctgcaa gccactggca agattcccga cctgccgacc gaggcgctga agccccagat   21180
catcacgggc atcgacgcga ttggccgagg ccaggatcaa gccaagctgt ccgccttcca   21240
agcgatgatc acgccctacg tggaccgtgt atccaaccgc gtggattggg acaacctgct   21300
gctgcgcgct gcgaacgcct ccgggatcga cccctctggg ctcatcctca cggaccagca   21360
gatgcagcaa cgtgcggccc aagagggcat cacgcagggc atggtccaag gcggcgctgc   21420
tgctggtcaa gccgctggtg ccaacctcgg cgctggtgct acggacccgg aagcgatggc   21480
cgctgcgatg ggctaataac ccacactaga ggtgaccctt cggggtccct catttccccc   21540
acttcaagga gaacacatgg aagttactgc aagcgacatc tacggctctg gcgcaatcgt   21600
ttcgtctggt gaactgacgg acgctgaacg tgccctgctg gacaacccgg cgagcatccg   21660
tgatggcgac gatgtgatcg acattcaggt cgagtccgag gacaagcccg atggtgactc   21720
cgaggaagtc caactggaca cctcgaaggg tgaccaagag ggtgaccaag aagaagaagt   21780
cgaagtggac cccgaaacgg gcctgccgac cgacgagaac atccagaagg gcatcaacac   21840
ccagcaggca gcgattggcg aacacgccca gaagatcgca gaagctggtc tcgacccggt   21900
tgctatcgtg gacgagtacc aagccaaggg cgcgctgtcg agcgccacct acgagtcgct   21960
ggaaaaggct ggctactcgc gggctgctgt ggacgcgatc atctcgggcc aagaagccca   22020
agcgcaactg ttcaaccagt cgatctactc cagcgtgggt ggtcaggccg gcttcacccg   22080
cgtggctgaa ttcgcccgca cgaacgaccc ggctggtgcc aaggcgtaca acgatgcgtt   22140
cgagcgtggc gatctggccg cgtgcaagtc gctgctgaag tcgttccaag ttcagatggg   22200
ccagaagtac ggcaccgcga acaagggcgt ccgtggcgcc aagcccgtaa cgcagggcac   22260
cgtgaaccgt gcgaagccgt tcgagtcgca gcaggacatg gtgaaggcga tgtccgacac   22320
gcgctatggc cgcgatgcga agtacaccgc cgaggtcgag cgacgcatca acgctggctg   22380
acgattaacc cacactatag gacagaggac gcagcaacag cacggcctcg aacctagaca   22440
tgactggctc gcttcggcgg gccttttctt tttcagatca aggagattca cacatggcaa   22500
ctaccgtaca aaatccgggt caagtcgcaa acgctggcga ccgtctggca ctgttcctga   22560
aggtcttcgc tggtgaagtc ctgaccgcct tctcgcgcac cgccaagtcg atggacaagc   22620
atatcgtccg cacgatccag tcgggcaagt cggcatcgtt cccggtgatg ggccgcactg   22680
tcggcaagta cctcgccccg ggcaactcgt tggacgacca cgcgcagcgcg attccgcaca   22740 acgagaagat catcgccatc gacggcctgc tgaccgctga cgtgctgatc acggacatcg   22800
acgacgcgat gaaccactac gatgtgcgcg gcgagtactc gaagcaactg ggcgaagcac   22860
tcgctctggc tgctgacggc tcggtgctgg ccgaactggc cgctctgtcg gctgtggccg   22920
agaacctgac gggtctgggc gccggtgcgc agatcgaact gaagaccgcc acctcggtgg   22980
ccgtggctga cccgaccgtt ggccaagaaa tcctggcctc gctggcgcag gctcgcatgg   23040
tgctgggcaa gaagtacgtc ccgaccgctg accgtgtgtt cttcgtgacg ccggaagcct   23100
actcctcgat cctcgctgcc ctgatgccgc aatcgagcaa ctaccacgcg atcatcgacc   23160
```

-continued

```
cggaaacggg caacctgcgc aacatccacg gcttcgagat catcgaagtg ccccactttg   23220
aactgggtgg cgcggatggc aagcacgcct tcccgcctgc actggctggc aaggtggtcg   23280
gtctggccgc tcaccgctcg gctgtgggca ccgtcaagct gaaggacctc gcactggaac   23340
gtgcccgccg tccggaattc caagccgacc agatcatcgc caagtacgcg atgggtcacg   23400
gtggcctgcg tccggaagcg gtctgcgctg tgctgaccaa ggctggcgcc taatcccgct   23460 ggggaccccct cgtgggtctc cgctggatcg caaccataaa gaacccctgt gggtcccttc   23520
ggggtctcat gggggttttt tcgcaactag gagaactcta tggcaaccat catcactccc   23580
cgcacggaac tcgatgcggt gaacgccatc atcggcgcta tcggtgaagg cgtggtgaac   23640
accttggagg gggacgctaa cgtggacgtg ctgaacgccc gtaggctcct cgctgtggtg   23700
tccgccgaga ttcaagataa gggctggggtg ttcaacactg acgaggcgtt cgagcttgtg   23760
cccgatacgt tctcgaacaa gatcgtttgg ctccccacgt acctccgcgt gatcaccccc   23820
ggggggaccc cctacgtgaa ccgtgggggc ttcgtctatg accggctggg ccgcaccgac   23880
cagttcacgg gccggatcac cgtcacgatg accgagcagg ttcccttcga ggaactgccg   23940
ctctgcttcc gccagtacat cacgtacacc gccgctgacc gcttcaacgc gcagtactac   24000
ggtgacccgg gcgtggaggc cgcgtgcaag caggccatcg tggagtcgtc acaagcggtg   24060
caggagtacg agattgatta tggcgggttc aacctgttca ataacgatcc gcactacctc   24120
gccaactctg ggaggtaacg atgccactcg tcacacaaac catcaagaac ctgaagggcg   24180
gcatctcgca acagccggac atcctacgct tccccgacca aggcgaggcc cagatcaacg   24240
gcttcagttc cgaggtcgag ggcttgcaga agcggccccc ttcggtccac gtcaagcgcc   24300
tgaccacgtt caccccgggg ctgaaaccgc tggtgaagct gatcaaccgg gacgagttcg   24360
agcggtactt cgtgtcgttc ctccccggtg ggtacatctc catcgtggac ctcgacggga   24420
acgccaagac ggtgaacacc cccaacggga ccggctacat caacagcgcg aatccccgcg   24480
aggacctccg catggtcacc gtggcggact acaccttcat catcaacaag aaggtgaccc   24540
cggcgctgga cggctcggtg gcctacccgg ggtatcgcac caacgggcag gcgctggtga   24600
acgtcaaggg cgggcagtac agccgcacct acagcatcga gttcaacggc ggggtgcagg   24660
ccagctacac gaccccggac ggctcggtgg cggcgcacgc ggcccagatt gacacccagt   24720
acatcgccca gcaattgggc aaccagcttg tgtccaactt ggggccgagc ggctggggcg   24780
tggacgtggg gccgaactac atcttcatcc aagcgcctag ctccaacagc gtgtggaacc   24840
tgaagattcg ggacggcttc aacaacggcc tgatgaccgg gtgcatcttc gaggtgcagc   24900
ggttcaacat gctgcccgcg caggcgcgtg atggctacat cgtcaaggtg ctgggcgacc   24960
ccggcagtgg ctcggatgac tactacgccc gcttcgacgt gggccgtggc gtgtgggcag   25020
agtgtgccgc cccgggctac caagggacgc tggccccgtg gtcaatgccg catgtgctgg   25080
tgcgcgaggc gaatggcacg ttcacgttcc gcgagcagac gtggcaggtc cgcccaagcg   25140
gggacattga ttcgagcccg gagccctcct tcgtggggac gcctatctcg gacgtgttct   25200
tcttccgcaa ccggctgggc gtgctggcgg gcgagaacgt gatcctgtcc gcatcgggcg   25260
agttcttcaa gttctggccc aagtccgtgg tcgctgccgc agacaccgat cccatcgacg   25320
tggcggtctc gcacagccgg gtctcgatcc tgcaccacgc ggtcccgttc gcggaggagt   25380
tgctgctgtg gtcggaccag acgcagttca tcctgaagtc ggacggcatc ctgtccacga   25440
agaccgtcaa ggtggacacc gcgaccgagt tcgagtcgag catcgacgcc cgcccggtgg   25500
```

-continued

```
ccgctggccg tggtgtgtac ttcgccgccc cgcgtgcgag cttcacctcg atccgccgct   25560
actacgcggt gcaggacacc tcgcaggtca agaacgccga ggacatctcc gcgcacgtcc   25620
cgagctacgt cccgaacggg gtgttcgcgc tgggatcgtc cacgactgag aacgtggtca   25680
cggtgctgac cgagggcgcc acgagccgca tctacctcta caagtacctc tacttgcaag   25740
agcaactggc gcagcagtcg tggtcccact gggacttcgg cccgggctcc gaggtgctgg   25800
cctgtgagat ggtcggggcg gtcatgtacc tgatgatcaa ttcccctcg gggacctacc    25860 tcgaatccat cgagttcacc cagaacacga aggactacga cttcgagccg ttccggttgc   25920
acatggaccg caagaagcaa gtggagaccc tgacgtacaa cctcgccacg aaccgcacgg   25980
tcatctcact ggcgaccgag tacggggcca cccccgcccg tgggaagtac tgggtggtga    26040
ccgaggacgg gcgcggctat gagttccccg agccggagac cggatgggta gcccaaggcg   26100
ggacgctgga gattcccggc gacctgacct cgaagacgat gctcatcggg gaggcgtaca   26160
cgttcaccta cacgatgtcc aagctgttga tcaaggtggc agacgcccaa ggggttcgct   26220
ccgaggacgt gggccgcttg cagattcagc gggcatgggt gaactacaac aactccggcc   26280
cgttcaccgt ggatgtgtgt gggaagttcc tctacaccat gagcggcaag aagctgggcg   26340
cctacgtgct gggcgaggac gcgctggata ccggccagtt ccgattcccg gtgatgacgg   26400
actcgcagcg gtgccgcgtg accatctcgt cggacaatcc tggccctgtg gcgatgattg   26460
gcgcgggctg gatcggcagg tatttccgcc gtgaacaggc gctgtgatgg ggcctgatta   26520
acccacacta taggaggggt ccctaaggaa aaccattaaa ggtaatccta aagggacccc   26580
ttctttcttt tcaactgaga ggagattacc aatcatgcgt ttgtatagcg aagacctgac   26640
cccgaagggc atcatcgagt tgatcgagca ggctctccct gaggataggc gcgagtatga   26700
gtgcctgact ggcaacccct tcgagtccct tgcggggtcc ctgatggact acctcgaaag   26760
cggcgcccat gcggaggccg tgcgggaccc ggagggcaac ctcgtggctg tcggcgggct   26820
ggaccatctc ggtgtctgct ggttcgtcac cacggcccga gtgaggtccc ataagggga    26880 cttctgcaag atcatcaagc accgcaggga tgtggtccac acggtctacg gggtcccctg   26940
cgtgaacatc gtcatgatgt ccaacgacct gcacgttcgg ttcctgcgtt atctgggggc   27000
cgagtttatc aacccagtca cgatcaacgg cgaggagttc cgcacgttcg tgatcaaacc   27060
gaggagcgac gatgtgtgaa ccagtaacca ttggtatggg catcatggcc gtggtcggca   27120
tggcgtccgc cgcttcggcc cagaaggacc aagcagacca gatcggtgat gcgcgtgcgg   27180
cccaagcggg gcaggcacgg caactgatca agcagatgaa ctacaaggac ggtcaactga   27240
atcaggagga ccgcaacgcc tacgagcagg cccagcagca actcgaaacg aactcgatca   27300
atgccatgcg caatcgaggg atgatcgagg ccgcgttcgc tgagtctggc gtggagggcc   27360
ggtcggtcga ttccgtgatc cgcgaggtca agggccaaga cgcccgcgtg gccgactcga   27420
tccgggccga ctacatgaac cagcgccgtg gcatccagtc tgcgtccgag cagaactaca   27480
tggagaccac tggggccatc tccgggcagg ccaagattcg cggcccgtcc aacgtgtccc   27540
agaccctgca agtcatcaat ggcgggatgc agggcgcgca ggcaggcgcc tcgatgggca   27600
atgcctattc cgcagcaacc gcgccgaagg gtacgccccc ggccaaaatc taaggaggtc   27660
acatgagcgc caatagtgca tacatgatgt ggcgccagtt ctccacgagc cctcgcgtgt   27720
cgaagggtgt cgaggctccg ggctaccgcg cccagtccgt acagaacact gtggacatgc   27780
gtggtcggag cactgcgggg attctggcgg acttcgccaa caacgcctcg caagcgttca   27840
acaccttcaa caaggtgcag tccgacgagg ccaacaccaa ggtccaggat tggatgaagg   27900
```

-continued

```
acaagacggt cgatgaatac cgcgccgaga tgaaggccgg taacgtcccg ttccaagacg   27960
accaagtggc aatggccgtg ctgcacaaca aggcggcata caccgctgcg ttgcaggtcg   28020
agcaggacgt ggaggaccag attcagcagg gcaagttcaa ggacttcaac gaggcggaca   28080
ccttccgcat caaggccctg aacagcgccc gcgccaagta cgccgagcag ttcaacctta   28140
ccccggacaa cgcggcgttc aaggctggct cgaccgggga ccaagagaag cgccgcgagg   28200
tgctgctgcg cctgcaaacg gacgtgacca ataagcgcct gcaacaagag ggcatgacgg   28260
tcgcggccac ggacctgatc gccccgctgc cggaagtgct ccagaacttc ggtgcggagg   28320
gtgcggccaa gtacatcatg cagaccacgg ccatgcacga caagaccggc ttggcccgca   28380
cggacgctga ccggctgacg ctgatcggga aggcggtcga ttccctgtcg gcctcgaagg   28440
gtggcgccga tgtgctcgaa caactgggcg ggcagacgat cagctacggc gggcaggacg   28500
tgaagctgcg cgacctgatg ggcggggggca agtttgacct cgctgtgatt caggcccgcc   28560
aagcggagaa cgcccgggac ggcgagcggt tcgtcaagca ggaggccgac tattccaact   28620
ggatggcgac caaggatgac accgccgcac agaagcacat cgaaacgctc ctgaaggaat   28680 cccgggggt ccgcaccct gaggtgaacc gagccacgga agtcctcggg ttcatcaaga   28740
agaagcagga gttcgaggcc cagcaggccc gcgagcagta cgccatgcag cttgagaagc   28800
agggccgcat tcagggcgca gtccggaccc tctcgggtgt cctctcgggg accatcacgg   28860
gcggcgtgtc ggctgaccct gacggcctcg gtctgaagga ccgcgaggaa ctggtcgctg   28920
ccgagaagat gatcgtggac gggctccctg agggtcccca gcgggacacc gccatcctga   28980
ggctagcctc gacggtcccc aatgggtacg ccttcaaggc cgtgaagggc atcgtggatt   29040
ccagcgaacg cgactgggaa ctcatgcagg cccagatcgc atccggcaag gcggacgtga   29100
aggttccacc ctcggtggag cgggtgcagg cgttcatgaa gctgggcgag ggttcctcgg   29160
tgctggctgt gaacaacggc aagcccccgg cctactggtc ggccatcgag gcaggcaccc   29220
ggatcggcgt gaccccggct gacgtggccg tgagtcaggc agcgtggaaa gccctcccgg   29280
agaaggagcg caacacgcgg atgcaggccc tgaccaagcc gctggcaaac ctgaacgtgc   29340
cgctgaacca gcgcaacgtg gagacattgc agacgttcgc gggccactac atggcgatgg   29400
gcctgtctgc cgagtctgct gcgaagcagg ccgagcagga cttccgggac cagaacgagg   29460
tcttcggcaa gggcaacggc gtggtccaca agtcgttctt ccagttcgac ggttcgcgta   29520
actcgttcgc cgctggccgc gccgcgttcg acggcatcct tgccgagacc cgcaacggat   29580
ggggcgtggg cgaggagcgc acgatgctgg actacagccc ggacagtcag caggtctcga   29640
tccgcaacgt gatgaccgga gagtcccggc ccgtcacgca ggacgatgtg cgggcgaagt   29700
acaagtatga cgctgagaag gccgcgaagg ccaacaaggc gaaggtggat gaaaccatca   29760
agcaggagtc ccaacgccag aagaagcgtt ccgaggttac cgccgaggac gtggcagcag   29820
cagcaggcgt gggaactgtc cgataaacctt tcaaggagat tcacatgacg acaaagtacg   29880
acgcgctgat cgagcaatcg gcgcaggcca acggtctcga cccggccaag ctgagggcgc   29940
agattcaagc ggagtcgaac ttcgacccgg ctgtggtctc caaagctggc gcagtcggca   30000
tcggccagat catgcccaag tactggatgg gtcagcacgg cctgaacagc atcgaggact   30060
tcaagaaccc agacaaggca atcccggcga tggccgctat catggcgcag aacgtgaagc   30120
aggccggaag ctgggagggc ggtctggtcc tctacaacgc gggcgcaggt aaggggaaca   30180
agtacctgaa cgccttcaag gccggtcagt atgacctgct gccggaggag acccgtggct   30240
```

-continued

```
acctcgggaa gctggcccc  tcgctgggga ttgcctcggg aaaagccccg ggcgtggtcg  30300
gcctcagtga tgcccgggtt gacctcaaca cgcccacaca ggtacagggg caggcactag  30360
ggcaatacag ggacctcaac gccgagcaag gactcggtga cagtttcctg tccggcctca  30420
acgcttctgc tattggcacc gctctgcgcc gttctgatag cccgatggct tcgctgctgg  30480
gcggctcgaa cccgctctcc gaagaagccc tgagcaagat tgccggggcc aacatcgggg  30540
ccagcgggac caagttcgtg atgcgcaacg ccatgaacga gcaacaggtc gatgaactga  30600
tcaaccttgc ccgggagaac caagcgagcg ccaaccagaa gcgaaccctc atgggtgacc  30660
tttcgtatgg cactggcgag atgctggggg accccgtgac gtatggcacg atggtgatcc  30720
cggctggggc cgctgtgaag gccgggcggc tgttctcgaa cggtatcgct cgggtggcct  30780 ctgcggggc  cgttgcggct gctgagggcg ctgcctcgaa cctagtgtcg gaagccttcc  30840
gggaatccac cacgggcaac gaggcggact tcgctggggc catcgcttcg ggtgccgcct  30900
tcgggctggg cctgcacggg ctcggcgtgg cgggtggctg ggcgtaccag aaggccgcga  30960
accggctgac ccgtggtatc caccgggccg aggcaggcga gactgtggcc gcgctccggg  31020
cggatgggca cacggacgca gtggacccga cgatcttcac gccgatggac atcgacaacg  31080
agaccgggat caagtggaag caaaccatcg accggggcga gttcaccgcc gcagaagcgg  31140
aagcccgccg tggcccgaac taccagccgg gtcaagtgcc ggtgctcctg aagacccccg  31200
ctggggacac cctgcacacg cccacgggca tccagttctc gtcggccaac ccactgaacc  31260
cgggccgagt cgaggccaac ctcgcaggcg ccccgctacc gttcgatggg gtggagattg  31320
gggacgttct gagccgcacc gagaaccaat ccctgaagga cctgttctgg aacctcggac  31380
ggtccacccg ggggtacacc gatgggtcct ccggcaagtt cggcgtgacg ggccaggatg  31440
tcgcccagaa catgaacggt cggttccacg actaccagtg gcaactcgat gcggcccgca  31500
cggaagccct tgcggagccc cagtgggtca acgccccggg gtcagcccga ggggtgcgcc  31560
aagcgttcaa cgagaagatt caacgggcga tgttcaagca ggacccctct gggctctcga  31620
aggccgaacg caaggtgtac gacttgcgca ccgagttcta ccgcgatctg gggcagcagc  31680
aggtcacccc gggggcacgg tggggcgtgg atgcgcccag cctgctggac gaggcgagct  31740
tcaagaagaa ctacggcgcc ccgatcatct atgacgatgt gaaggtgcgc gccctgacgg  31800
accagatcgg tgcggacgcc ttgcaggacc tcgtggcccg cagcttcatc ggctcctacc  31860
tgtcgaaccc ggaggtgcgt aaggccgtga tcgagcgcat cgcgcaggac gcagcgcagg  31920
gcatccagcg ggacttccgg caactggcgc acgacatcgc ctacgggatt gtgaagtcag  31980 gcgaccgct  ggacggcgtg ggcgtgtctc acctgaaccg catcatggat tcgggcgtgg  32040
gccatgccga ctccaccccg ggcttccgca agcaacgcaa cccgttcggc catgactacg  32100
agattgaggt ccccggccag cagggcaagt tcagcgtggc ggacctgttc agctacgaca  32160
cggacctgat cgacacgggg tacttcaacc gcgtgcgcgg cgatgtgtct ctgagtgtgg  32220
gcgctggcgc tgggctgtcg gacgtgacgg acatcatccg ttcggcgcgg gagttcgcag  32280
gcgcggtggc cccggagcag aaggccgctg tggacgctgc cgagatgctg gtcaaccaac  32340
tctacggggt cggcatgaac agcgactggg cgcggcttcg tgcggtcgag ggcatcgtca  32400
agaacctcgc cttcatgaag tcgtccgcgt tcatgggcct gtccaactac accgagattg  32460
cggcaggcat ccgcgagcac ggcatctcgt ttgcggccaa gtctatcccg ggcgtgggca  32520
agctgttctc gaacctgatg aacggcaaga ccacggaagc gaacatgcga ctggcgcagg  32580
gtctggtctg gggccgggaa ctggacaagg cgatcatccc ctcgttcagc gaggccatcg  32640
```

-continued

```
agcgcagcgt ggacaacctg agtgaccgca tcggggaggg catcaccgcc tccgcactgg   32700
gcgggatcaa gggcgcgacc gaggctgctg ccgacaagtg gtgggcgacc aagttcctgc   32760
gggcgaccag tggtcgcatc gtggagactg cgcgggccga gttcttcgcg gacctcgccc   32820
gtggggcgca cactggcaag tcgagcttcg ccaacgtgac caaggccaag gccgcgtccg   32880
tgagtcccga gcaactgaac ggggtgctgg acctgctgcg tgaatcgacc cagatcgtgg   32940
acggtgaact gaaggtgacg aacccgaagg cactgaccga cgatccccgg gccgctgcac   33000
tgcgccgcta tgggcagtac tggtcggagc gggtgatcca gcagaacacg gtctcgtcaa   33060
ccttccgctg ggccggtatg ccggtggtcg ggatgctgtc gcagttccag tcgttcgtga   33120
tgcgctcggt gaatgccaag ctgatccgag ggaccgctgc gacgttccgc gatggggatg   33180
tgggtcaggg catcgacacc ttcatcctcg ggccggtgct ggcggggctc ggctacgccg   33240
ggatgacgta cctgcgcgcc cagaagttca gcaacgaggc agaccgccag aagtacctcg   33300
aagaaaacct cggggagaag ggcgactact cgatgctggt ggcgggctcc ctgaagcgtt   33360
ccgccgcgtt cggcgccatc ggcaacctgc acgacaccgt ggtgtccacc cctctggtgg   33420
cccagtgggc gcccgactac agcgccaagt atgcgggcct tgggcggacc tcacaggagg   33480
ccaagctgag gcgtgaccgg cagagtgccc agcagggcgc ccctgtgggg aacctcctcg   33540
gcggcatcgt gcagaacgcc ccggctgtga agctggcgga ttccctcgcg gggctcgcgt   33600
gggcacccgt ggatcgtctg acgaccccgg ctgactcctt tgacgaggac cgctggcata   33660
agggcgtggt gcgctccatg aagggcctcg tgcccaacga tccggtctcc cagcgggcat   33720
tccaagagtg gatcgctgac ccgtactgac cgggagatta acccacactg taggacatag   33780
gctggccctt cggggctggc ctttttttcg ttaaccgata aggaggacac acatggctgc   33840
accaacaacc gtgaaggtct atccgctgaa taacgttgtc aaggacttcc ccattgactt   33900
cgattatctg gcccgtgagt tcgtcgtggt gaccctgctg gggaacggcc gccgcgaact   33960
ggtccagaac agcgagtaca ccttcctgag tgccacgcag attcgcacga ccgccacttg   34020
gggtcccgcg cagggctacg acaacatcga ggtccgccgc gtgaccagcg ccgagaaccg   34080
gctggtgacg ttcaatgacg cctcgatcct gcgggccgct gacctgaacc tcgcggaact   34140
gcaaacggtc cacatcgcac aggaggcccg cgatctggtc tcggatgcgc tgggtacgaa   34200
tgacgatggc aacctcgatg cacgcaaccg ccgcatcgtg aacctcggca acccggtcga   34260
tccgcaggac gcgatgacca aggactacta cgactcgcgg ctcggtgagg ccaagacgtg   34320
gcgcgacgaa acgttaactg cccgcgatgc gaccttcacc gcccgggaca ccacgctagg   34380
ctaccgcgac acgaccctga cgtacaagaa cgctgccgag gcggcgcgtg acgctggctt   34440
tgcggcccgt gacgtggcac tcgctgcgcg ggacaccacg ctcggctacc gcgacacggc   34500
caaccaacac cgcatcgacg cgcaagcggc ccgcgatctg gcgctccagt atcgcaacga   34560
ggccgaggcg ttcaagaaca ctgccagcga caaggcagac atcgtgctga ccatcgaggc   34620
cacggccaac tctgctaagg cggaagccca agcggcgacc gctgccacga ccggcctgat   34680
ggacaacgac ctgcaactgt tcgtgaacgg cacccagcgc cgcgacatca aggtcaaggc   34740
gggcaagcat gacgcccaag gcgttcaacg tgcaggtgtc cgcttcactg acgttggacac   34800 catcgctgtc gagcggtaca accagaccac gggcgtgatc atcgacactc cggtgaagat   34860
cgaccaagcg accggggatg tcgtgctcgc gtccaagaag atcaagggcg tgaccactcc   34920
cacggccaac gacgaagcgg ccaacaagag ctacgcggac accaagctgc cgttcgtcgg   34980
```

-continued

```
aggcaccta accgggtctc tgttcgtgag tggcgcgacc gacaacgctg gggccttccg   35040
ggtcacggct gacctcggcg gtgcgtgggt ggattggaac gcggcacgca agtacccgct   35100
ccagatcgac tgccccgcct cctccgctgc ctacggcggc atccggtgga cacgctgggg   35160
cgcccgccat atcgccgcaa ttgacgcctt cgacaacacc ggaggcgccc cagtaatcgt   35220
gatgcacctt ggcgaccaga acaatgcgtg gtcgttctac aaggacaaca tctaccgggg   35280
gtacaacggc ggctacgtgt ggggctcgtg gaacttcaac ccggccagca aggcgaacgc   35340
cgactggatc accgatgttg gcatcgaggg gaacgacatc cgccgcccct acgttcgacg   35400
cgccagcgat ggctacatcg tccggatgcc ccgcaacttc tccggcaacg cgctggaggt   35460
gggctgggat ggtggcctgc ggtggtacgt ggatggggtc caccaaggcg cgatggtcag   35520
cgatacgaac tggcgcggcg cgttccacaa cgacgcgggc cggatcggac gcggcggtga   35580
ctggtccatc ggcaacggct acttcgacgt ggtgatcgac ggggtttcct acggggtccc   35640
cttcaatccc tcggatgctc gccgcaagga gaacatcgtg ccgtccaccg aggacgccat   35700
cgagaaggtg aagcagatca agttctactc cttcaacttc aaggcggatg gcctgatgga   35760
ctccaagaag gtccaccaga ctggcttcat cgcgcagcag cttcagggtg ttgatccggc   35820
gctggtgatc ggtgacgaca acccggatat gaccctctcg cctgacgtga actcgctcct   35880
gtcgctggcc ctgaagtcca tccagcaact cgacgcgaag atcgcagtgc tggaggagac   35940
catcctggcc ctcaaaggta acccctgatg agaccccagc gcgtccgtat caatgggcgc   36000 cgctggacccc ttgagtaccc cgaagcgata gacgacgagg gcacctacgg gatcacctac   36060
tacgacaccc acacgatcca agtgcgggac ggtctggctc ccatcgagga ggccgacacg   36120
gtgatccatg aagtgctcca cgccctcatc gcttcgatgg gcctcacggt gcccgacgag   36180
gagcccatcg tgcgcgccct cgcctcgggg ctcaccgggg tcctagcgga taaccccacg   36240
ctcctgaagc acctgaacgg gtgcctgaag gggtcccccca agaaggagaa gtaatggtca   36300
atctcgacgt tcaaaacggg atcgtccagt ttgccccgcc cgccgtggta gccggagagg   36360
ttgcctcgcg ggtgctgggc ctgacgatca atgagtggtt ctacatcgtg gcgatcatct   36420
gcatgttgat cagcaccgtc acgacatccc tcgtggcgtt cattaagtct cgcaagaagg   36480
atgacaacaa gaaggaggac gaatgagcaa gctagaagaa ctgctttccc agattcacct   36540
cgaagtcgcg cagcagatgc ttgccgacct gcgggacgag gagaagcgca cccccgcgct   36600
ctacaacgcg atcatcaagt tcctgaagga caacggcgtg gaaatcgagc cgaagtcccc   36660
ggaggagaag aaccgagagg ccgctgagaa gtccagcgcg gcccagatcg cggccctgtc   36720
ccaagaactc ccgcccgtgc tggcggatga cgagggcttc gcccaattcc attaacccac   36780
actagaggag cttccctatg tccatcgagc aactgaaggc ggacacccgg gaagccctgc   36840
tgcaaaagcg tatgcgcgac gacttccgag tcttcgtgtg gttcgtctgg aaggtgatca   36900
acctcccgaa tcccacggcg attcagaacg acatggcgct cacgctccag aacccgccct   36960
cgcggcgctt catcttgcag ggtttccgtg gtgtggctaa gtcgttcatc acctgcgcct   37020
atgtggtctg gcgcttgtgg cgcgacccgc aactcaaaat catgatcgtg tcggcctcga   37080
aggaacgcgc cgatgcgaac tcgcagttca tcaagaagat catctcggaa atcgagttcc   37140
tgcatcacct caaggcgaag ccgggacaag tagacaccgt ggtgaaattc gacgtaggcc   37200
cgaagctgcc tgaccactcg ccctcggtga agtcggtcgg tatcacgggc cagcttaccg   37260
gctcccgcgc tgacatcatc atcgcggatg acgtggaggt cccgggcaac agttcgaccc   37320
aaggcgcccg cgacaagctg tttgaactcg tcaaggagtt cgacgctatc ctgaagccgg   37380
```

```
gtgggacggt catctatctg ggcacgcctc agaacgagat gtcgctctac aacgaactgc   37440
tgaaccgtgg ctacaccacg ctgatctggc ccgcccggta tccgcgtgac gagaagcagc   37500
gggccaacta cggcacccgc ctcgccccgt atctcgcgga gcggtacgac gctgacccgg   37560
atggcctcgc gtggaagccc acggacccgg aacgctttga cgagaaggac ctgcttgaac   37620
gtgaggtctc ctacggcaag gctggcttcg cgttgcagtt catgctcgac acctccctgt   37680
cggacgccga gaagtacccg ctccggttgc gcgacatgat cgtcggcctg ttccccaagg   37740
agcgagcccc aatggcgcac gactggcttc ctggccctac cttggagctt ggcaaccttc   37800
cgcagatcgg gctcaagggt gaccgctact acggcgccta tggctcgtcc aaggagatgt   37860
ccaactactt cggcaaggtt ctcgccatcg accctcgggg gcgcggcaag gacgagaccg   37920
gctatgccgt gatgtacttc ctgaacggct acctctatct gatggaggtg ggcggcttcc   37980
ggggcggcta cgaggactcg acgctggagg aactggcgaa ggtcgccaag aagtggaacg   38040
tgaacgatgt catcatcgag ggtaacttcg gggacggcat gtacctgaag ctgtttacgc   38100
ccttcctgca ccgcatccac aagtgctcgg tcgaggaaat caagtcggtc ggccagaagg   38160
aggtccggat cgcggacgtg ctggagccga tcttcggcgc ccatcggttc tgcgtgagcg   38220
agtccgccat cgagcacgac tacgcgaccg ccaaggacgt ggacggcaag ttcgacccga   38280
agtactcgtg cttctaccag atgtcccgcc tgacccgcga acgcggcgcg ctggcccatg   38340
acgaccgctt ggacgctgtg gcgatggccg ctgccttctt cgtggagcgc atggacctcg   38400
acgcggccaa gcagattcag gaggccaccg aggagttcat cgcggcccac atggaggacc   38460
ccttgaggac cggcgagcac ctgacgcggt acatcgacgg gggtgacggg atggtgatcc   38520
tgtcgagcga ggaccgagt gacgactact ggggcgaccc caacatgctt gacgcggatgac   38580 catataggtg cctgagaggg ttccggctac agatcatgac aaaattgatct aaggctggaa   38640 cccttgctgg tggccggtct ccgggtgtgt caagaactat ttcgattaac ccacactata   38700 gaggggggagc cccggtaagg tatatacagt ggccctccca acatgagacc agcaggcact   38760
agaaggagcc ctctagggtt cccgctgggg gcctatgctg atctgctctc tgtgcaatat   38820
caatcattgg atcaacatca taaaggaggt gatcatggac aaggtgaaga ctgtgttgaa   38880
ggctgtcctg cgtgacaagc ggtttttggg cctcgttgct gtggccgtgg ctggcttggg   38940
cgtcagtgtc gtacctgctg gcaccatcga agctgttggc tgcgctctgg ctggcggctg   39000
tgtgtgaagc ggtggcgcgt gctgccgccc ggaaggttcg ctgaatcgct caccttccgg   39060
gaattacaag tgggatgaac tggaggggac cctctagtgt cccatcttgt gtccctgctg   39120
tggctgtcct tgtggtgacc ctgcggggga acacctgagg ggccaggacc tgagggaccc   39180
caaaaggtgt acaggtagga aaaatctgag agggtatctc atagaatgag ccgctgggat   39240 taccccata gggggtccac ttgggccact ggggcaggca ggaggccccc ccgggtgccc   39300
ctctcggcac tccctgaggg gaaccggcag ggtcaaccca ctggatttaa cataatggac   39360
cttatgcgca atccctatag gtcacattga gggtactgat aggggctctc tatgggctcc   39420
tctggggtga taggagggct ctatgggttt cccta                             39455
```

BACTERIOPHAGE, BACTERIAL WILT DISEASE CONTROL AGENT, AND BACTERIAL WILT DISEASE CONTROL METHOD

CROSS-REFERENCE TO RELATED APPLICATIONS

The present application is the national stage of international application PCT/JP2020/029189, filed on Jul. 30, 2020.

TECHNICAL FIELD

The present invention relates to a bacteriophage, a bacterial wilt disease control agent and a bacterial wilt disease control method.

BACKGROUND ART

*Ralstonia solanacearum* infects 200 plant species or more such as the Solanaceae plants and causes bacterial wilt. When the disease progresses, the plant infected with *Ralstonia solanacearum* withers.

Major chemical pesticides which have been used so far against bacterial wilt are chloropicrin and bromomethane, which are powerful drugs.

In view of the problems such as the increase in the effective application amounts, the environmental pollution, the ozone layer depletion, the influences on the health and the pesticide residues, however, development of safe alternative pesticides and control techniques which replace the chemical pesticides is desired.

Although techniques using bacteriophages (PTLs 1 to 3) have been known so far as safe alternative pesticides and control techniques which replace the chemical pesticides for example, the techniques are effective against a limited number of *Ralstonia solanacearum* strains, and a technique which is effective against a wider variety of *Ralstonia solanacearum* strains has been desired.

CITATION LIST

Patent Literature

PTL 1: JP-A-2007-252351
PTL 2: JP-A-2018-24589
PTL 3: WO2017/104347

SUMMARY OF INVENTION

Technical Problem

Accordingly, a problem of the invention is to provide a bacteriophage which is effective against a wider variety of *Ralstonia solanacearum* strains and a bacterial wilt disease control method using the bacteriophage.

Solution to Problem

As a result of extensive studies to solve the problem, the present inventors have found that a bacteriophage in which the amino acid sequence at the C-terminus of a tail fiber protein including a host recognition site is a specific sequence infects a wide variety of *Ralstonia solanacearum* and thus have completed the invention.

That is, the invention is a bacteriophage characterized in that the amino acid sequence at the C-terminus of a tail fiber protein including a host recognition site is the amino acid sequence of SEQ ID NO: 1 and that the bacteriophage infects *Ralstonia solanacearum.*

Moreover, the invention is a bacterial wilt disease control agent characterized by containing the bacteriophage as an active component.

Furthermore, the invention is a bacterial wilt disease control method in a plant characterized by administering the bacterial wilt disease control agent to a plant or a plant growth medium.

Further, the invention is the amino acid sequence at the C-terminus of a tail fiber protein including a host recognition site shown in SEQ ID NO: 1 and a base sequence encoding the amino acid sequence.

Advantageous Effects of Invention

The bacteriophage of the invention infects a wide variety of *Ralstonia solanacearum* strains and thus is effective for controlling bacterial wilt.

Moreover, by incorporating (or substituting with) the amino acid sequence at the C-terminus of a tail fiber protein including a host recognition site of the invention (SEQ ID NO: 1) into a host recognition site of a tail fiber protein of another bacteriophage or the like by a general method using the amino acid sequence or a base sequence encoding the amino acid sequence, infection of a wide variety of *Ralstonia solanacearum* strains is enabled.

DESCRIPTION OF EMBODIMENTS

Figure 1:
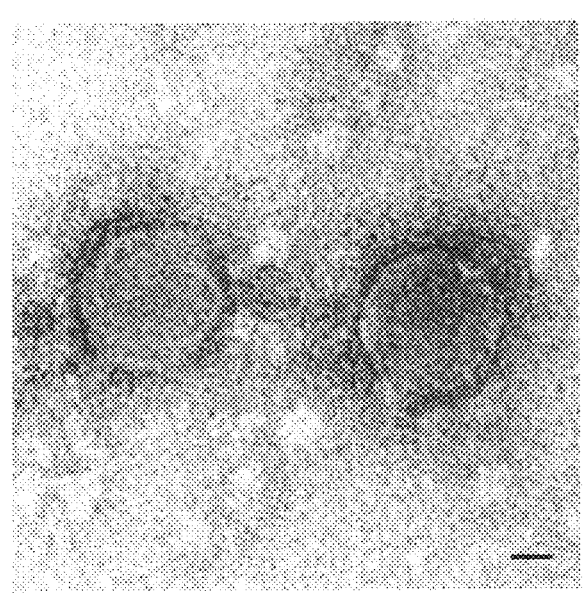
FIG. 1 shows an example of the appearance of bacteriophage RKP181 of the invention. The length of the bar in the figure is 20 nm.

The amino acid sequence at the C-terminus of a tail fiber protein including a host recognition site of the bacteriophage of the invention is the amino acid sequence of SEQ ID NO: 1, and the bacteriophage infects *Ralstonia solanacearum.*

The amino acid sequence at the C-terminus of a tail fiber protein including a host recognition site of the bacteriophage shown in SEQ ID NO: 1 is largely different from the amino acid sequences at the C-terminus of a tail fiber protein including a host recognition site of conventionally known bacteriophages, and as a result, the bacteriophage infects a wide variety of *Ralstonia solanacearum* strains. For example, the identities of the amino acid sequences at the C-terminus of a tail fiber protein including a host recognition site of RSJ5 and RSB2, which are related bacteriophages of the bacteriophage of the invention, to the amino acid sequence at the C-terminus of a tail fiber protein including a host recognition site of the bacteriophage of the invention are only 38% and 23% according to ClustalW analysis (see the Examples).

As described above, the bacteriophage of the invention infects a wide variety of *Ralstonia solanacearum* strains because the amino acid sequence at the C-terminus of a tail fiber protein including a host recognition site is the amino acid sequence of SEQ ID NO: 1.

Here, by incorporating (or substituting with) the amino acid sequence at the C-terminus of a tail fiber protein including a host recognition site of the invention (SEQ ID NO: 1) at a host recognition site of a tail fiber protein of another bacteriophage or the like by a general method using the amino acid sequence or a base sequence encoding the amino acid sequence, infection of a wide variety of *Ralstonia solanacearum* strains is enabled (Document 1. (Ando H, Lemire S, Pires D P, Lu T K. 2015. Engineering Modular Viral Scaffolds for Targeted Bacterial Population Editing. Cell Systems 1:187-196.)). The base sequence encoding the amino acid sequence at the C-terminus of a tail fiber protein including a host recognition site (SEQ ID NO: 1) which the bacteriophage of the invention has is not particularly limited as long as the base sequence corresponds to the amino acid sequence but is preferably the sequence from the 34, 313th to the 35, 968th residues of the base sequence of SEQ ID NO: 3 (the whole genome sequence of RKP181)

The *Ralstonia solanacearum* infected with the bacteriophage of the invention is not particularly limited as long as the *Ralstonia solanacearum* is any of those found from 200 plant species or more such as the Solanaceae plants, the Zingiberaceae plants and the plants, the Lamiaceae but bacteriophage infects at least all of strain MAFF107624, strain MAFF211266, strain MAFF211270, strain MAFF211543, strain MAFF301859, strain MAFF311644, strain MAFF730103, strain MAFF730131, strain MAFF302745, strain MAFF311632, strain MAFF211536, strain MAFF331041, strain MAFF730139, strain MAFF211280, strain MAFF211533, strain MAFF211468, strain MAFF211516, strain MAFF311101, strain MAFF311102, strain MAFF211479, strain MAFF211471, strain MAFF211483, strain MAFF211484, strain MAFF211486, strain MAFF211272, strain MAFF211276, strain MAFF211278, strain MAFF211490, strain MAFF211492, strain MAFF211497, strain MAFF211476, strain MAFF211414, MAFF211429 strain strain and MAFF301558 and further infects the 70 *Ralstonia solanacearum* strains or more collected by the present inventors. In this regard, the *Ralstonia solanacearum* strains having a number with MAFF can be obtained from Genebank Project, NARO, Agriculture National and Food Research Organization.

In this regard, the infection here refers to the state in which plaques are formed on an agar plate on which *Ralstonia solanacearum* grows or the state of lysing in a liquid medium in the presence of RKP181.

The bacteriophage of the invention described above can be obtained by screening known bacteriophages according to a general method to find those in which the amino acid sequence at the C-terminus of a tail fiber protein including a host recognition site is the amino acid sequence of SEQ ID NO: 1.

Moreover, the bacteriophage of the invention should have the above amino acid sequence. Thus, the bacteriophage of the invention may belong to any group, any order or any family but preferably belongs to the family Podoviridae of the order Caudovirales of the group I.

The bacteriophage of the invention has a head diameter of 30 to 90 nm, preferably 55 to 66 nm, a tail length of 5 to 30 nm, preferably 11 to 17 nm and a width of 5 to 20 nm, preferably 10 to 17 nm.

The bacteriophage of the invention has a double-stranded genome.

The genome size of the bacteriophage of the invention is not particularly limited but is for example 6,000 to 280,000 bp, preferably 38,000 to 40,000 bp. The genome size is the value of the whole genome base sequence.

The GC content of the bacteriophage of the invention is not particularly limited but is for example 55 to 75%, preferably 61 to 64%. The GC content is the value calculated from the whole genome base sequence.

The number of genes in the bacteriophage of the invention is not particularly limited but is for example 10 to 330 genes, preferably 50 genes. Of the 50 genes, 49 genes are in the same direction.

The genomic DNA of the bacteriophage of the invention is preferably digested into fragments through treatment with the restriction enzyme Eco81I, particularly preferably into five fragments of 2 kb or more. The conditions for treatment with the restriction enzyme Eco81I are at 35 to 40° C. for one to three hours.

Furthermore, the bacteriophage of the invention may have, for example, genes such as lysozyme and typeII holin or may have a circular or linear genome.

A preferable example of the bacteriophage of the invention explained above is RKP181 found by the present inventors. RKP181 was deposited for an international deposit at NITE Patent Microorganisms Depositary, National Institute of Technology and Evaluation (address: #122, 2-5-8 Kazusakamatari, Kisarazu-shi, Chiba 292-0818, Japan) on Mar. 27, 2020 under NITE BP-03186.

The bacteriophage of the invention also includes those having modification, mutation or the like while maintaining the properties.

Because the bacteriophage of the invention can infect a wide variety of *Ralstonia solanacearum*, a bacterial wilt disease control agent can be obtained using the bacteriophage as an active component.

In this regard, the control here refers to suppression and alleviation of infection of a plant with *Ralstonia solanacearum*, suppression and alleviation of the onset of bacterial wilt by *Ralstonia solanacearum*, suppression and alleviation of spread of infection with bacterial wilt disease or control of *Ralstonia solanacearum*.

The amount of the bacteriophage of the invention in the bacterial wilt disease control agent may be appropriately set depending on the purpose of control, but for example, the bacteriophage of the invention may be contained at potency of $10^3$ to $10^{12}$ pfu/mb, preferably $10^5$ to $10^{11}$ pfu/mL.

The bacterial wilt disease control agent may contain only the bacteriophage of the invention, which is the active component, but may further contain another substance, a composition of the like such as an agronomically, pharmacologically and botanically acceptable protein stabilizer.

The bacterial wilt disease control agent described above can control bacterial wilt disease in a plant when administered to a plant or a plant growth medium. Examples of the plant include tomatoes, eggplants, bell peppers and tobaccos of the family Solanaceae, *Perilla frutescens* var. *crispa* and

*Perilla frutescens* of the family Lamiaceae, ginger, turmeric and curcuma of the family Zingiberaceae and the like. The plant growth medium may be soil, a solid medium such as a mat containing organic materials, a liquid containing a nutrient solution or the like. The method and the conditions for administering the bacterial wilt disease control agent to such a plant or a plant growth medium are not particularly limited but are, for example, spraying or dropping to the plant or the plant growth medium, injection into the plant or the like.

EXAMPLES

The invention is explained in detail below referring to Examples, but the invention is not limited to the Examples.

Example 1

Separation of Bacteriophage:

Soil was suspended in water and then left still, and thus a supernatant was obtained. The supernatant was filtered with a filter of 0.25 μm, and the filtrate was subjected to a plaque assay using *Ralstonia solanacearum* as the host. By isolating a formed plaque, bacteriophage RKP181 was obtained.

Example 2

Analysis of Bacteriophage RKP181:
(1) Electron Microscope Analysis

A phage suspension of $2\times10^{11}$ pfu/ml was stained with 1% uranyl acetate, and pictures were taken under an electron (JEM-1400Pus, manufactured by JEOL Ltd.).
(2) Determination of Genome Size The genomic DNA was prepared from the phage particles by phenol/chloroform extraction. To determine the size of the genome, the purified genomic DNA was subjected to agarose gel electrophoresis with Mupid-2plus electrophoresis apparatus (manufactured by Mupid) using 0.3% agarose (Agarose H, manufactured by Nippon Gene Co., Ltd.). Moreover, the genomic DNA which was treated with restriction enzymes EcoRI the (manufactured by Toyobo Co., Ltd.) and Eco81I (manufactured by Takara Bio Inc.), respectively was subjected to agarose gel electrophoresis with Mupid-2plus electrophoresis apparatus using 0.8% agarose (Agarose 1200 Standard Type, manufactured by PH Japan Co., Ltd) or 0.3% agarose (Agarose H, manufactured by Nippon Gene Co., Ltd.).

According to the bands of the size marker, the genome size of RKP181 was estimated to be 38,400 to 48,500 bp. Moreover, as a result of comparison with the bands of the size marker, the band sizes obtained by the treatment with EcoRI were 21.1 kb, 16.1 kb, 1.3 kb and 1 kb, and the band sizes obtained by the treatment with Eco81I were 12.9 kb, 10.2 kb, 7 kb, 6.3 kb and 2 kb, which means that there were five fragments of 2 kb or more. It was thus found that the genome size of RKP181 is 38.4 to 39.5 kbp.
(3) Determination of Genomic Structure The purified genomic DNA was treated with a single-stranded DNA nuclease (S1 Nuclease, manufactured by Promega Corporation), a DNA nuclease (Recombinant DNase I, manufactured by Takara Bio Inc.), an RNA nuclease (RNase A, manufactured by Takara Bio Inc.) and a linear DNA nuclease (BAL31 nuclease, manufactured by New England Biolabs, Inc.) and subjected to electrophoresis by the method described in the above Example. Moreover, the terminal structures of the genome were determined by treating the genomic DNA which was treated with the linear DNA nuclease (BAL31 nuclease) for different time periods with Eco81I (Takara Bio Inc.) and conducting electrophoresis by the method described in the above Example.

Figure 2:
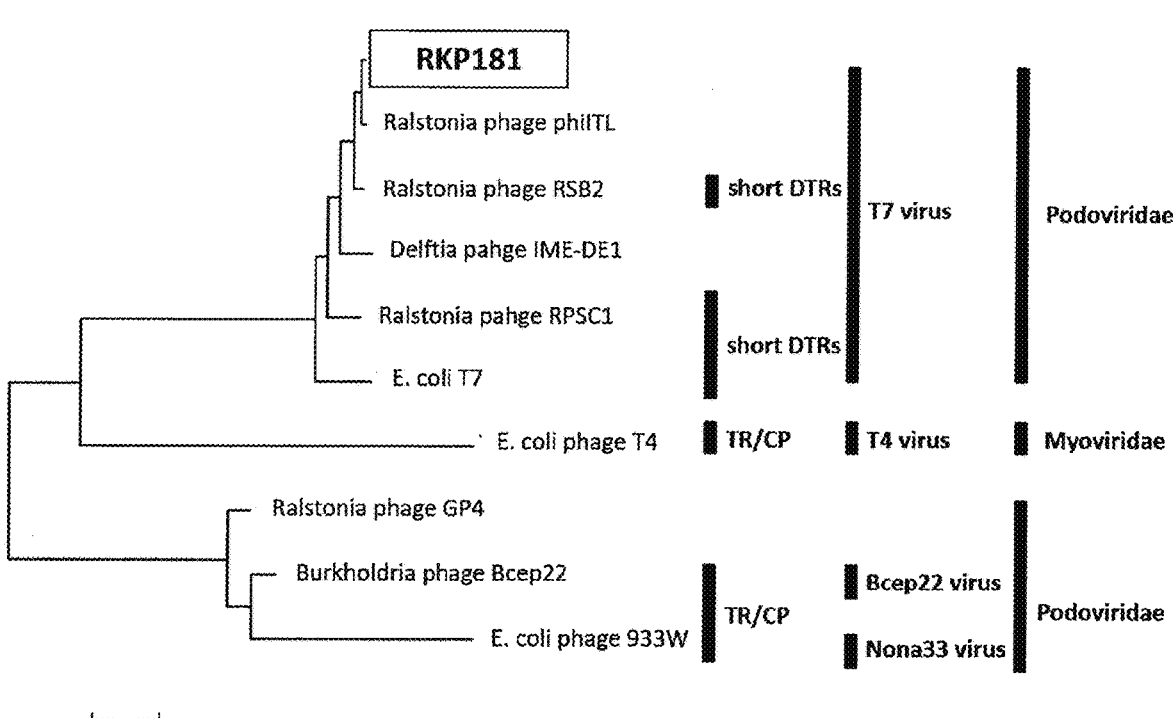
FIG. 2 shows a phylogenetic tree (Maximum Likelihood) based on the amino acid sequence of the DNA packaging protein B gene of RKP181.

Because the genomic DNA of RKP181 was not digested with the single-stranded DNA nuclease (S1 Nuclease) and the RNA nuclease (RNase A) but was digested with the DNA nuclease (Recombinant DNase I) and the linear DNA nuclease (BAL31 nuclease), it was found that the genome of RKP181 is linear double-stranded DNA. Moreover, the fragments of 12.9 kb, 10.2 kb, 7 kb, 6.3 kb and 2 kb obtained by the treatment with Eco81I were lost with time with the linear DNA nuclease (BAL31 nuclease) from the fragments of 10.2 kb and 6.3 kb,
(4) Genomic Analysis The whole genome base sequence of RKP181 was determined with PacBio RS II (manufactured by PACIFIC BIO-SCIENCES), The determined base sequences were assembled using RS_HGAP Assembly 2.3.0. To estimate the terminal structures and the lengths of the terminal sequences of the genome, PhageTerm (Galaxy) was used. The terminal redundant sequences were determined by Sanger sequencing (Applied Biosystems 3730xl DNA analyzer). Related strains based on the whole genome sequences were searched by homology search with BLASTN (Table 1). The open reading frames (ORFs) were estimated using MetaGeneAnnotator 1.0 of MiGAP ver2.23 (Database Center for Life Science), tRNAscan-SE 1.23 and BLAST 2.2.18 (Table 2). The functions of the detected ORFs were estimated using the COG, Refseq, TrEMBL and nr databases for those at the top obtained by homology search with MiGAP/BLAST and PSI-BLAST (Table 2). The molecular phylogenetic tree based on the amino acid sequences of the DNA packaging protein B gene was created by the maximum likelihood method by obtaining the amino acid sequences of the DNA packaging protein B gene of the related strains from the NCBI database and aligning the sequences with ClustalW of MEGA 7.0.26 (FIG. 2).

The genome had a size of 39, 455 bp and contained redundant sequences at both ends, and the terminal redundant sequences were 239 bp in length. The GC content of the genome was 62.6%. From the identity comparison of the genomes, RKP181 was related to phages of the genus 7-like virus of the family Podoviridae (podovirus) of the order Caudovirales, which is consistent with the results of the electron microscope analysis (Table 1 and FIGS. 1 and 2). The closest related strain was known *Ralstonia* phage strain phiITL-1 (Table 1 and FIG. 2), and the identity was 87% (coverage of 84%) according to BLASTN. The next homologous strain was *Ralstonia* phage strain RSB2 (coverage of 70% and identity of 77%). From the results of the analysis with PhageTerm and the phylogenetic systematic analysis based on the DNA packaging DNA protein B gene (FIG. 2), the terminal structures of the genome of RKP181 were estimated to have a short direct terminal redundancy [short DTR] structure and to be T7 type as described above. The whole genome of RKP181 determined with PacBio RS II is shown in SEQ ID NO: 3. Moreover, as shown in Table 2, the genome of RKP181 included 50 genes in total, of which 49 genes were in the same direction.

TABLE 1

| Top | Accession | Species | Coverage | Identity | Family | Genus | Structure | Base Length (b) | GC (%) | Gene Number |
|---|---|---|---|---|---|---|---|---|---|---|
| 1 | KP343639.1 | *Ralstonia* phage phiITL-1 | 84% | 87% | Podoviridae | T7 virus | Circular | 38,731 | 62.8% | 54 |
| 2 | AB597179.1 | *Ralstonia* phage RSB2 | 70% | 77% | Podoviridae | T7 virus | Linear | 40,411 | 61.8% | 53 |
| 3 | KR153873.1 | Delftia phage IME-DE1 | 6% | 75% | Podoviridae | T7 virus | Circular | 38,084 | 60.4% | 48 |
| 4 | MF893341.1 | *Ralstonia* phage RPSC1 | 3% | 74% | Podoviridae | T7 virus | Circular | 39628 | 61.6% | 43 |

TABLE 2

| ORF | Start (nt) | End (nt) | Length (nt) | Length (aa) | strand | putative function | organism | product | E-value | Ident. | homolog accession no. |
|---|---|---|---|---|---|---|---|---|---|---|---|
| DTR | 1 | 239 | 239 | NA | + | direct terminal repeat | NA | NA | NA | NA | NA |
| 1 | 404 | 634 | 231 | 76 | – | Signal transduction histidine kinase | *Ralstonia* phage phiITL-1 | hypothetical protein | 3E−39 | 84% | AJT60839.1 |
| 2 | 1,304 | 1,504 | 201 | 66 | + | NA | *Ralstonia* phage phiITL-1 | hypothetical protein | 4E−30 | 76% | AJT60799.1 |
| 3 | 1,769 | 2,011 | 243 | 80 | + | NA | *Ralstonia* phage phiITL-1 | hypothetical protein | 2E−34 | 70% | AJT60800.1 |
| 4 | 2,022 | 2,441 | 420 | 139 | + | Cell division protein FtsI/ penicillin-binding protein 2 | *Ralstonia* phage RSB2 | hypothetical protein ORF3 | 5E−58 | 63% | YP_009017724.1 |
| 5 | 2,519 | 2,764 | 246 | 81 | + | Non-ribosomal peptide synthetase modules and related proteins | *Ralstonia* phage RSB2 | hypothetical protein ORF4 | 5E−35 | 70% | YP_009017725.1 |
| 6 | 2,820 | 3,002 | 183 | 60 | + | NA | *Ralstonia* phage RSB2 | hypothetical protein ORF5 | 1E−14 | 52% | YP_009017726.1 |
| 7 | 2,999 | 3,178 | 180 | 59 | + | NA | *Ralstonia* phage RSB2 | hypothetical protein ORF6 | 8E−16 | 65% | YP_009017727.1 |
| 8 | 3,175 | 3,495 | 321 | 106 | + | Uncharacterized bacitracin resistance protein | *Ralstonia* phage RSB2 | hypothetical protein ORF7 | 2E−26 | 59% | YP_009017728.1 |
| 9 | 3,492 | 3,857 | 366 | 121 | + | Phosphoenol-pyruvate carboxykinase (GTP) | *Ralstonia* phage RSB2 | hypothetical protein ORF8 | 1E−49 | 72% | YP_009017729.1 |
| 10 | 3,870 | 4,049 | 180 | 59 | + | NA | *Ralstonia* phage phiITL-1 | hypothetical protein | 6E−06 | 48% | AJT60804.1 |
| 11 | 4,075 | 4,341 | 267 | 88 | + | NA | *Ralstonia* phage phiITL-1 | hypothetical protein | 1E−37 | 73% | AJT60805.1 |
| 12 | 4,320 | 4,586 | 267 | 88 | + | Ribonucleases G and E | *Ralstonia* phage phiITL-1 | hypothetical protein | 1E−39 | 78% | AJT60806.1 |
| 13 | 4,651 | 5,007 | 357 | 118 | + | NA | *Ralstonia* phage phiITL-1 | hypothetical protein | 4E−46 | 85% | AJT60808.1 |
| 14 | 5,058 | 5,466 | 408 | 135 | + | Enoyl reductase domain of yeast-type FAS1 | *Ralstonia* phage phiITL-1 | hypothetical protein | 1E−42 | 77% | AJT60810.1 |
| 15 | 5,489 | 5,570 | 102 | 33 | + | NA | *Ralstonia* phage RSB2 | hypothetical protein | 1E−12 | 91% | YP_009017736.1 |
| 16 | 5,567 | 6,499 | 933 | 310 | + | ATP-dependent DNA ligase | *Ralstonia* phage phiITL-1 | ATP-dependent DNA ligase | 7E−110 | 54% | AJT60812.1 |
| 17 | 6,496 | 6,615 | 120 | 39 | + | NA | *Spirosoma spitsbergense* | M56 family metallo-peptidase | 0.5 | 49% | WP_020605153.1 |
| 18 | 6,768 | 9,365 | 2,598 | 865 | + | Mitochondrial DNA-directed RNA polymerase | *Ralstonia* phage RSB2 | DNA-directed RNA polymerase | 0E+00 | 80% | YP_009017739.1 |

TABLE 2-continued

| ORF | Start (nt) | End (nt) | Length (nt) | Length (aa) | strand | putative function | organism | product | E-value | Ident. | homolog accession no. |
|---|---|---|---|---|---|---|---|---|---|---|---|
| 19 | 9,385 | 9,831 | 447 | 148 | + | NA | *Ralstonia* phage phiITL-1 | hypothetical protein | 4E−57 | 59% | AJT60815.1 |
| 20 | 10,012 | 10,257 | 246 | 81 | + | NA | *Ralstonia* phage phiITL-1 | hypothetical protein | 9E−05 | 53% | AJT60816.1 |
| 21 | 10,254 | 10,553 | 300 | 99 | + | Flp pilus assembly protein TadC | *Ralstonia* phage phiITL-1 | hypothetical protein | 5E−24 | 62% | AJT60817.1 |
| 22 | 10,616 | 10,921 | 308 | 101 | + | NA | *Ralstonia* phage phiITL-1 | hypothetical protein | 2E−60 | 89% | AJT60818.1 |
| 23 | 10,914 | 11,609 | 696 | 231 | + | AraC-type DNA-binding domain-containing proteins | *Ralstonia* phage RSB2 | hypothetical protein ORF23 | 6E−93 | 68% | YP_009017744.1 |
| 24 | 11,590 | 11,763 | 174 | 57 | + | deoxynucleoside monophosphate kinase | *Ralstonia* phage phiITL-1 | hypothetical protein | 7E−17 | 67% | AJT60821.1 |
| 25 | 11,831 | 12,496 | 666 | 22 | + | NA | *Ralstonia* phage phiITL-1 | Putative ssDNA binding protein | 1E−138 | 91% | AJT60822.1 |
| 26 | 12,499 | 12,966 | 468 | 155 | + | single-stranded DNA-binding protein | *Ralstonia* phage phiITL-1 | T7-like phage endonuclease | 2E−105 | 94% | AJT60823.1 |
| 27 | 12,968 | 13,438 | 471 | 156 | + | Formamido-pyrimidine-DNA glycosylase | *Ralstonia* phage RSB2 | lysozyme [Peplidoglycan recognition proteins] | 5E−61 | 63% | YP_009017748.1 |
| 28 | 13,545 | 15,230 | 1,586 | 561 | + | lysozyme(N-acetylmuramoyl-L-alanine amidase) | *Ralstonia* phage phiITL-1 | DNA primase/helicase-like protein | 0E+00 | 90% | AJT60826.1 |
| 29 | 15,240 | 17,348 | 2,109 | 702 | + | Replicative DNA helicase | *Ralstonia* phage phiITL-1 | DNA polymerase" | 0E+00 | 95% | AJT60827.1 |
| 30 | 17,398 | 17,775 | 378 | 125 | + | DNA polymerase I - 3'-5' exonuclease and polymerase domains | *Ralstonia* phage phiITL-1 | hypothetical protein | 8E−56 | 78% | AJT60828.1 |
| 31 | 17,798 | 17,998 | 201 | 56 | + | NA | *Pectobacterium* phage PPWS4 | HNS binding protein | 2E−18 | 55% | ATN92966.1 |
| 32 | 17,995 | 18,879 | 885 | 294 | + | Glycosyltransferase | *Ralstonia* phage phiITL-1 | phage exonuclease | 0E+00 | 95% | AJT60830.1 |
| 33 | 18,901 | 19,212 | 312 | 103 | + | 5'-3' exonuclease (including N-terminal domain of PolI) | *Ralstonia* phage phiITL-1 | hypothetical protein | 7E−36 | 67% | AJT60831.1 |
| 34 | 19,226 | 19,591 | 366 | 121 | + | Fe2+ transport system protein B | *Ralstonia* phage phiITL-1 | hypothetical protein | 3E−63 | 76% | AJT60832.1 |
| 35 | 19,594 | 19,896 | 303 | 100 | + | Uncharacterized conserved protein | *Ralstonia* phage phiITL-1 | hypothetical protein | 2E−27 | 82% | AJT60833.1 |
| 36 | 19,901 | 21,496 | 1,596 | 531 | + | Small-conductance mechanosensitive channel | *Ralstonia* phage phiITL-1 | Putative head to tail joining protein (collar) | 0E+00 | 92% | AJT60834.1 |
| 37 | 21,557 | 22,381 | 825 | 274 | + | Transcriptional regulators | *Ralstonia* phage phiITL-1 | Putative capsid assembly protein | 1E+00 | 84% | AJT60835.1 |
| 38 | 22,494 | 23,453 | 960 | 319 | + | Phage T7 capsid assembly protein | *Ralstonia* phage phiITL-1 | Putative major capsid protein | 0E+00 | 93% | AJT60836.1 |
| 39 | 23,560 | 24,138 | 579 | 192 | + | major capsid protein | *Ralstonia* phage phiITL-1 | Putative tail tubular protein A | 8E−123 | 87% | AJT60837.1 |
| 40 | 24,141 | 25,507 | 2,367 | 788 | + | T7 tail tubular gp11 protein | *Ralstonia* phage RSB2 | Putative tail tubular protein B | 0E+00 | 80% | YP_009017762.1 |
| 41 | 26,615 | 27,079 | 465 | 154 | + | FOG: WD40 repeat | *Ralstonia* phage phiITL-1 | Putative internal virion protein A | 2E−104 | 94% | AJT60786.1 |

TABLE 2-continued

| ORF | Start (nt) | End (nt) | Length (nt) | Length (aa) | strand | putative function | organism | product | E-value | Ident. | homolog accession no. |
|---|---|---|---|---|---|---|---|---|---|---|---|
| 42 | 27,072 | 27,653 | 582 | 193 | + | Putative internal virion protein A | Ralstonia phage phiITL-1 | Putative internal virion protein B | 2E−108 | 87% | AJT60787.1 |
| 43 | 27,663 | 29,846 | 2,184 | 727 | + | Putative internal virion protein B | Ralstonia phage phiITL-1 | Putative internal virion protein C | 0E+00 | 83% | AJT60788.1 |
| 44 | 29,865 | 33,749 | 3,885 | 1,294 | + | Putative internal virion protein C | Ralstonia phage phiITL-1 | Putative internal virion protein D | 0E+00 | 88% | AJT60789.1 |
| 45 | 33,833 | 35,958 | 2,136 | 711 | + | Soluble lytic murein transglycosylase and related regulatory proteins (some contain LysM/invasin domains) | Ralstonia phage RSJ5 | putative phage tail fiber protein | 4E−107 | 42% | YP_009218128.1 |
| 46 | 35,968 | 36,294 | 327 | 108 | + | Phage T7 tail fibre protein | Ralstonia phage phiITL-1 | Putative uncharacterized protein | 4E−68 | 96% | AJT60793.1 |
| 47 | 36,294 | 36,506 | 213 | 70 | + | AraC-type DNA-binding domain-containing proteins | Ralstonia phage phiITL-1 | Putative lysis protein | 4E−35 | 84% | AJT60794.1 |
| 48 | 36,503 | 36,775 | 273 | 90 | + | type II holin | Ralstonia phage phiITL-1 | Putative packaging maturation protein A | 4E−35 | 84% | AJT60794.1 |
| 49 | 36,798 | 38,579 | 1,782 | 593 | + | DNA packaging protein, small subunit | Ralstonia phage phiITL-1 | Putative packaging maturation protein B | 0E+00 | 94% | AJT60797.1 |
| 50 | 38,795 | 39,007 | 213 | 70 | + | NA | Ralstonia phage phiITL-1 | hypothetical protein | 5E−20 | 77% | AJT60798.1 |
| DTR | 39,217 | 39,455 | 239 | NA | + | Direct terminal repeat | NA | NA | NA | NA | NA |

(5) Genetic Map

Figure 3:
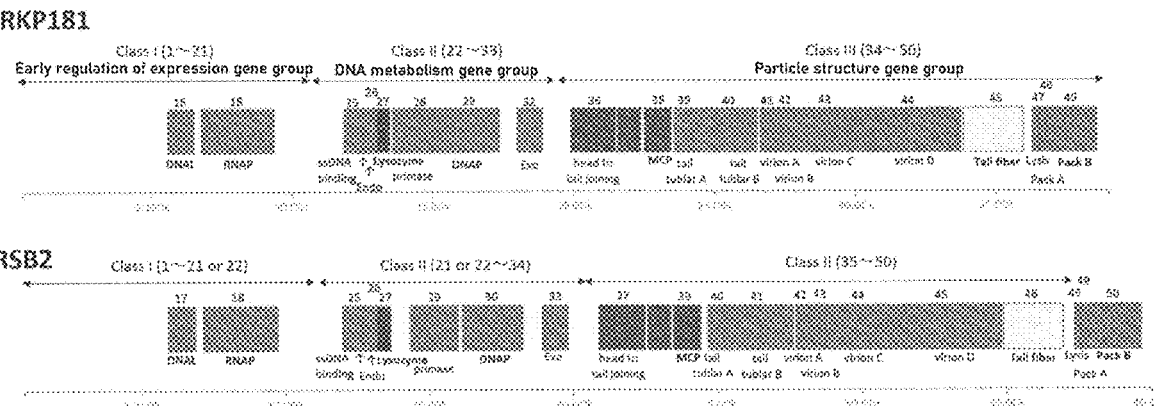
FIG. 3 shows comparison of the maps of major genes of RKP181 and RSB2.
Figure 4:
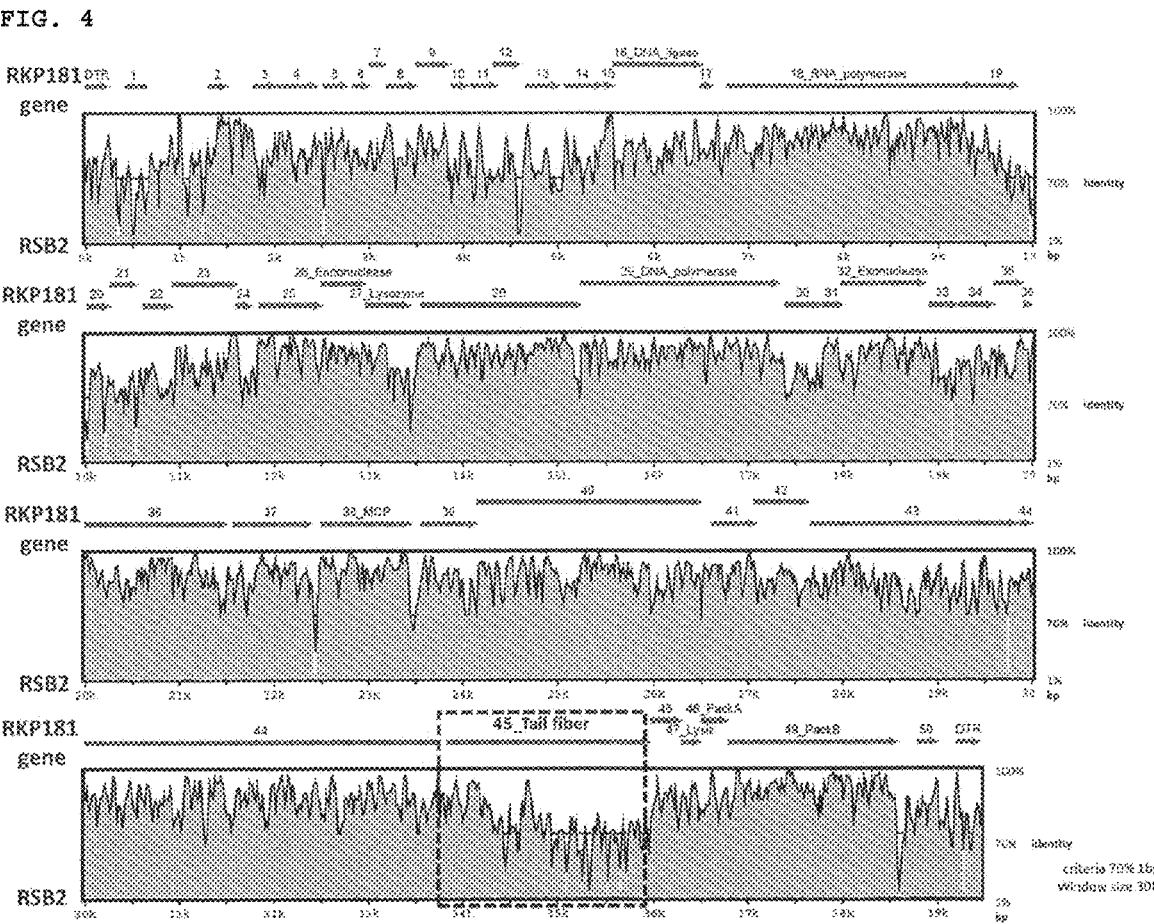
FIG. 4 shows comparison of the whole genome sequences of RKP181 and RSB2.

Maps of major genes in the genomes were drawn using PHASTER, and RKP181 and Ralstonia phage RSB2 (AB597179.1) of JP-A-2018-24589 were compared (FIG. 3). Moreover, the entire base sequences were also compared using comparative genomic software LAGAN (FIG. 4).

As in RSB2, the genome of RKP181 included three distinct function modules of class I, class II and class III (FIG. 3, Document 2 (Kawasaki T, Narulita E, Matsunami M, Ishikawa H, Shimizu M, Fujie M, Bhunchoth A, Phironrit N, Chatchawankanphanich O, Yamada T. 2016. Genomic diversity of large-plaque-forming podoviruses infecting the phytopathogen Ralstonia solanacearum. 492: 73-81.) Virology and Document 3 (JP-A-2018-24589)). Moreover, because the T-type RNA polymerase gene (RNAP) is in class I in the genome of RKP181 as in RSB2, it is believed that the infection cycle period is shorter than those of other bacteriophages due to rapid expression of RNA polymerase like RSB2 (FIG. 3, see below).

Although the whole genome base sequence and the genetic map of RKP181 are similar to those of RSB2, regarding the tail fiber gene, the identity of ORF45 of RKP181 and the homolog of RSB2 is significantly low (see below), (6) Analysis of Tail Fiber Protein-Encoding Gene (Tail Fiber Gene)

Figure 5:
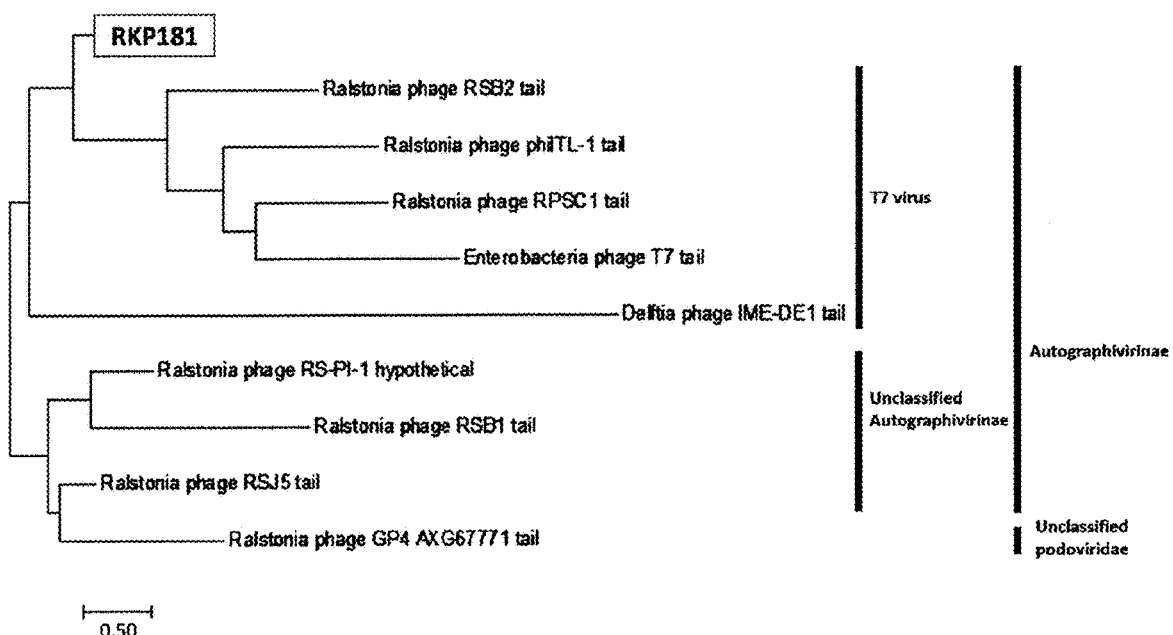
FIG. 5 shows a phylogenetic tree (Maximum Likelihood) based on the amino acid sequence encoded by the tail fiber gene of RKP181.
Figure 6:
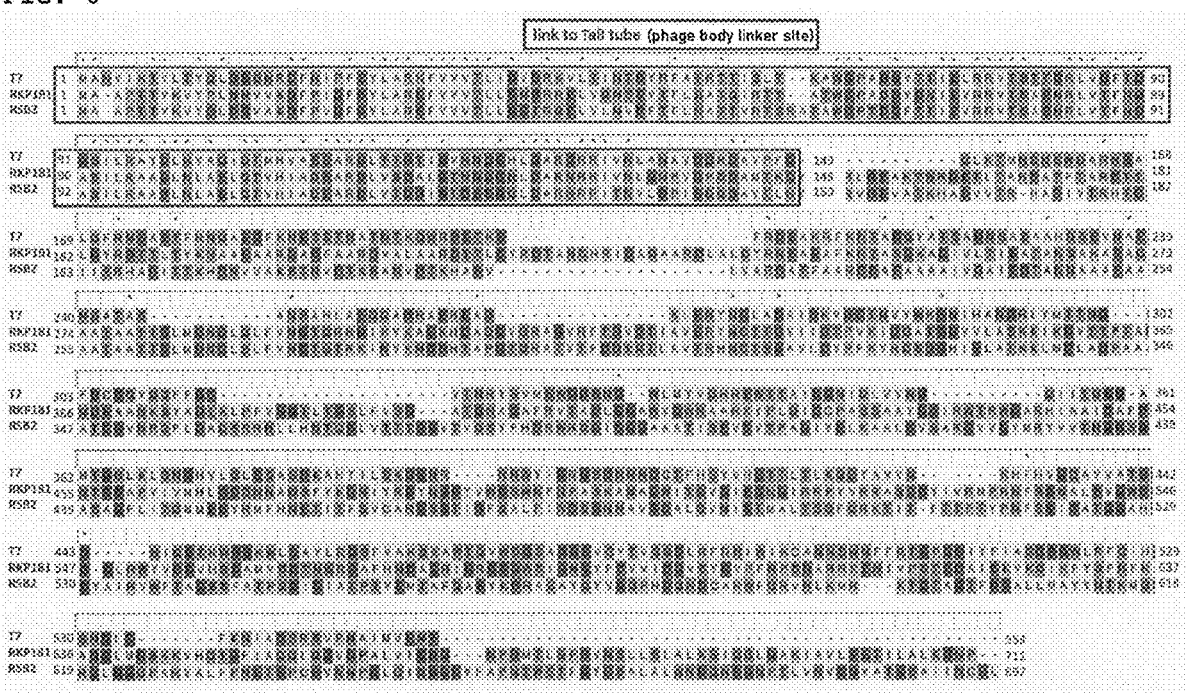
FIG. 6 shows comparison of the identities of the tail fiber gene products of RKP181, T7 and RSB2.

Homology search of the amino acid sequence of ORF45 (SEQ ID NO: 2) encoded by the tail fiber gene of RKP181 was conducted using BLASTP (Table 3). Moreover, the amino acid sequence of ORF45 and known homologous tail fiber gene products were aligned with ClustalW of MEGA 7.0.26, and a molecular phylogenetic tree was created by the maximum likelihood method (FIG. 5). Further, the domains of ORF45 were searched using BLASTP. The identity comparison of the sequence of the 1-149th amino acids of the phage body (tail tube) linker site of the tail fiber gene (AAM43540.1) of T7 and the 1-148th amino acids of ORF45 (shown in SEQ ID NO: 2) of RKP181 was conducted with BLASTP. Subsequently, homology search of the two identified domains, namely, the sequences of the 1-160th amino acids at the N-terminus and the 161-711th amino acids at the C-terminus, was conducted with BLASTP (Table 4 and Table 5). The identities of the tail fiber gene products of RKP181, T7 and RSB2 were compared by obtaining the sequence (BAJ51834.1) of the tail fiber gene (ORF46) of RSB2 and the sequence (P03748.1) of tail fiber gene gp17 of T7 from the NCBI database and comparing the identities using ClustalW of MEGA 7.0.26 (FIG. 6).

As a result of the homology search with BLASTP, the identity of ORF45 of RKP181 to the tail fiber protein of Ralstonia phage RSJ5 was the highest (coverage of 64% and identity of 42%) (Table 3). Moreover, the identity to the tail fiber protein of Ralstonia phage RSB2 was 53% (coverage of 53%), and the identity to the tail fiber protein of Ralstonia phage phiITL-1 was 85% (coverage of 22%). The identity to the tail fiber protein of Enterobacteria phage T7 was 42%

(coverage of 37%). Furthermore, when the identities of the full-length tail fiber proteins were compared by the analysis with ClustalW, the identity of ORF45 of RKP181 to the tail fiber protein of RSJ5 was 38%, and that to the tail fiber protein of RSB2 was 23%, which were found to be significantly lower than the identities obtained by the base sequence comparison of the whole genomes (Table 1). The analysis results show that the amino acid sequence of ORF45 (shown in SEQ ID NO: 2) encoded by the tail fiber gene of RKP181 is unique (see below).

the phage body (tail tube) linker site of the tail fiber gene (AAM43540.1) of T7 and the 1-148th amino acids of ORF45 (shown in SEQ ID NO: 2) of RKP181. When BLASTP search was conducted using the sequence of the 1-148th amino acids of ORF45 of RKP181, the identities to the homologous sites of the tail fiber proteins of *Ralstonia* phage phiITL-1 and *Ralstonia* phage RSB2 were 85% (coverage of 100%) and 73% (coverage of 100%), respectively. Furthermore, as a result of the analysis using BLASTP and ClustalW, the identities of the 1-160th amino

TABLE 3

| Top | Protein | Species | Coverage | Identity | Accession |
|---|---|---|---|---|---|
| 1 | putative phage tail fiber protein | *Ralstonia* phage RSJ5 | 64% | 42% | YP_009218128.1 |
| 2 | putative tail fiber protein | *Ralstonia* phage RSB2 | 53% | 53% | YP_009017767.1 |
| 3 | putative tail fiber protein | *Ralstonia* phage phiITL-1 | 22% | 85% | AJT60790.1 |
| 4 | tail fibers protein | *Escherichia* phage 64795_ec1 | 37% | 43% | YP_009291518.1 |
| 5 | tail fiber protein | *Escherichia* phage C5 | 38% | 43% | AYD80209.1 |
| 6 | hypothetical protein | *Ralstonia solanacearum* | 67% | 32% | WP_064049197.1 |
| 7 | tail fiber protein | *Escherichia* phage HZ2R8 | 65% | 44% | AUV62662.1 |
| 8 | tail fiber protein | *Pectobacterium* phage PP74 | 34% | 44% | APD19655.1 |
| 9 | tail fiber protein | Enterobacteria phage T7 | 37% | 42% | AAM43540.1 |
| 10 | hypothetical protein | *Pseudomonas chlororaphis* | 20% | 64% | WP_053269386.1 |

As a result of the comparison of the identities based on the whole genome sequences, RKP181 was related to T7-like bacteriophages, RSB2 and phiITL-1 (Table 1), and similar results were obtained from the molecular phylogenetic analysis based on the amino acid sequences of the DNA packaging protein B gene (FIG. 2). When a molecular phylogenetic tree was created using the amino acid sequences of the tail fiber gene, however, RKP181 belonged to a different clade from that including RSB2, phiITL-1 and T7 unlike in FIG. 2 (FIG. 5).

acids of ORF45 of RKP181 were largely different from those of the subsequent sequence at the C-terminus (Tables 4 and 5). In other words, the 1-160th amino acids at the N-terminus of ORF45 of RKP181 had an identity of 85% (coverage of 99%) to the homologous region of the tail fiber protein of phiITL-1, an identity of 72% (coverage of 99%) to that of RSB2 and an identity of 58% (coverage of 89%) to that of T7 (Table 4).

TABLE 4

| Top | Protein | Species | Coverage | Identity | Accession |
|---|---|---|---|---|---|
| 1 | putative tail fiber protein | *Ralstonia* phage phiITL-1 | 99% | 85% | AJT60790.1 |
| 2 | putative tail fiber protein | *Ralstonia* phage RSB2 | 99% | 72% | YP_009017767.1 |
| 3 | hypothetical protein | *Pseudomonas chlororaphis* | 92% | 64% | WP_053269386.1 |
| 4 | Phage tail fibers | *Yersinia* phage fPS-59 | 96% | 57% | SOO46827.1 |
| 5 | putative tail fiber protein | *Erwinia* phage pEp_SNUABM_09 | 90% | 59% | QEQ94708.1 |
| 38 | tail fiber protein | *Escherichia* phage T7 | 89%% | 58% | AAM43534.1 |

The tail fiber gene of bacteriophage T7 has a phage body (tail tube) linker site at the 1-149th amino acids at the N-terminus and has a host recognition site (tip domain) at the 465-553rd amino acids at the C-terminus (Document 4 (Steven A C, Trus B L, Maizel J V, Unser M, Parry D A D, Wall J S, Hainfeld J F, Studier F W, 1988. Molecular substructure of a viral receptor-recognition protein: The gp17 tail-fiber of bacteriophage T7. J Mol Biol 200:351-365.) and Document 5 (Garcia-Doval C, Raaij M J van. 2012. Structure of the receptor-binding carboxy-terminal domain of bacteriophage T7 tail fibers. PNAS 109:9390-9395.)).

When the domains of ORF45 of RKP181 were searched using BLASTP, the tail fibre protein (pfam03906) of T7 and the chaperone domain (pfam13884) of a phage protein, endosialidase were identified. Regarding the tail fibre protein (pfam03906), an identity of 58% (coverage of 96%) was detected between the sequence of the 1-149th amino acids of As described above, the N-terminus side of the tail fiber protein, which is the phage body (tail tube) linker site, was widely conserved among known bacteriophages and especially was a domain with a high identity between RKP181 and related bacteriophages. On the other hand, the domain at the C-terminus involving in the host recognition varied among the bacteriophages. The bacteriophages that have a tail fiber gene in which the chaperon domain (pfam13884) of endosialidase is located at the C-terminus and that infect *Ralstonia solanacearum*, like RKP181, were RSJ5 and RS-PI-1 only. Moreover, when homology search was conducted with BLASTP using the sequence of the 161-711th amino acids of RKP181 excluding the phage body linker site, the identities of the C-terminus side involving in the host recognition were significantly lower than those of the N-terminus side of the phage body (tail tube) linker site, with an identity of 42% (coverage of 83%) even to the most homologous tail fiber protein of RSJ5 and an identity of 35% (coverage of 60%) to the tail fiber protein of RS-PI-1 (Table 5). Similarly, the identity to the tail fiber protein of RSB2, which does not have the chaperon domain (pfam13884), was significantly low, namely 51% (coverage of 17%).

TABLE 5

| Top | Protein | Species | Coverage | Identity | Accession |
|---|---|---|---|---|---|
| 1 | putative phage tail fiber protein | *Ralstonia* phage RSJ5 | 83% | 42% | YP_009218128.1 |
| 2 | hypothetical protein | *Ralstonia* solanacearum | 64% | 35% | WP_064049197.1 |
| 3 | hypothetical protein WK94_23500 | *Burkholderia ubonensis* | 61% | 37% | KVW40325.1 |
| 4 | hypothetical protein | *Burkholderia ubonensis* | 59% | 37% | WP_143135316.1 |
| 5 | hypothetical protein | *Ralstonia* solanacearum | 88% | 31% | WP_049842194.1 |
| 6 | hypothetical protein | *Burkholderia ubonensis* | 58% | 37% | WP_060368006.1 |
| 7 | hypothetical protein | *Burkholderia ubonensis* | 58% | 37% | WP_060063309.1 |
| 8 | hypothetical protein | *Burkholderia ubonensis* | 58% | 37% | WP_059841529.1 |
| 9 | hypothetical protein | *Burkholderia ubonensis* | 58% | 37% | WP_060032179.1 |
| 10 | hypothetical protein | *Burkholderia ubonensis* | 58% | 37% | WP_060163429.1 |
| 11 | hypothetical protein | *Burkholderia ubonensis* | 58% | 37% | WP_059872146.1 |
| 12 | hypothetical protein | *Ralstonia* phage RS-PI-1 | 60% | 35% | AQT27772.1 |

(7) Summary

From the above results, it was found that bacteriophage RKP181 has the following properties.

RKP181 is classified to the genus 77-like virus of the family Podoviridae (podovirus) of the order Caudovirales.

The genome of RKP181 is linear double-stranded DNA.

The genomic structure is type 17 having a short direct terminal redundant sequence structure.

The genome size is 39,200 bp to 39,500 bp, preferably 39,455 bp (including two terminal redundant sequences) or 39,216 bp (including one terminal redundant sequence).

The ends of the genome may have a terminal redundant sequence of 200 to 250 bp, preferably 239 bp.

The GC content is 62.6%.

The closest related strain of known strains is *Ralstonia* phage strain phiITL-1, with an identity of 87%. The next closest strain is *Ralstonia* phage strain RSB2, with an identity of 77%.

The amino acid sequence at the C-terminus of a tail fiber protein including a host recognition site is the amino acid sequence of SEQ ID NO: 1.

Example 3

Separation and Control of *Ralstonia solanacearum:*

(1) Separation from Disease Plant

A stem of a disease plant was cut, and bacterial ooze was collected. The bacterial ooze was appropriately diluted with distilled water. The diluted solution was applied to Modified SMSA medium, and formed colonies was separated onto CPG agar plates (10 g of peptone, 1 g of casamino acid, 5 g of glucose and 1.7% agar per 1 L).

(2) Separation from Soil

Soil and water were mixed well and left still, and then the supernatant was separated. The separated supernatant was appropriately diluted with water, and the diluted solution was applied to Modified SMSA medium. Formed colonies was separated onto CPG agar plates.

<Modified SMSA Medium (per 1 L)>

| | |
|---|---|
| Peptone | 10 g |
| Glucose | 5 g |
| Casamino acid | 1 g |
| Agar | 18 g |
| Bacitracin (10 mg/mL) | 2.5 mL |
| Polymyxin B sulfate (50 mg/mL) | 2 mL |
| Chloramphenicol (10 mg/mL) | 0.5 mL |

-continued

| | |
|---|---|
| Penicillin G potassium (1 mg/mL) | 0.5 mL |
| Crystal violet (1 mg/mL) | 5 mL |
| Tetrazolium chloride (10 mg/mL) | 5 mL |

(3) Results

One strain of *Ralstonia solanacearum* was separated from one field by the above method, and 70 *Ralstonia solanacearum* strains or more in total from the hosts of the family Solanaceae, the family Zingiberaceae, the family Lamiaceae and the like were separated.

Example 4

Examination of Host Range of RKP181:

(1) Presence or Absence of Infection

The presence or the absence of infection was examined by a plaque assay or a spot test.

(2) Plaque Assay

The *Ralstonia solanacearum* strains were cultured at 28° C. overnight in CPG medium (10 g of peptone, 1 g of casamino acid and 5 g of glucose per 1 L). The bacterial culture was adjusted to $OD_{600}$ of 0.25 with CPG medium. A serial dilution of a phage solution was prepared. The bacterial solutions and the diluted phage solutions were mixed and left at 28° C. After 30 minutes, the bacterium/phage mixtures were mixed with 3 ml of top agar (3 g of peptone, 0.3 g of casamino acid, 1.7 g of glucose and 5 g of agar per 1 L) and layered onto CPG agar plates. After culturing at 28° C. overnight, the presence or the absence of infection was observed with the presence or the absence of plaques.

(3) Spot Test

Culture solutions of the *Ralstonia solanacearum* strains which were cultured at 28° C. overnight in the CPG medium were adjusted to $OD_{600}$ of 0.25 with CPG medium. The bacterial solutions in a volume of 250 μL and 3 ml of top agar were mixed and layered onto CPG agar plates. After top agar was hardened, a phage solution was spotted, and the presence of the absence of plaques was observed to examine the presence or the absence of infection, (4) Results It was found that RKP181 infects all the 100 *Ralstonia solanacearum* strains or more in total from the hosts of the family Solanaceae, the family Zingiberaceae, the family Lamiaceae and the like separated from the nature, including the 34 strains listed in Table 6, which can be obtained from Genebank Project, NARO, National Agriculture and Food Research Organization (Tsukuba, Ibaraki),

17

TABLE 6

| Bacterial Strain | Source of Separation |
|---|---|
| MAFF107624 | Tomato |
| MAFF211266 | Tomato |
| MAFF211270 | Tomato |
| MAFF211543 | Tomato |
| MAFF301859 | Tomato |
| MAFF311644 | Tomato |
| MAFF730103 | Tomato |
| MAFF730131 | Tomato |
| MAFF302745 | Tomato |
| MAFF311632 | Tomato |
| MAFF211536 | Tomato |
| MAFF331041 | Tomato |
| MAFF730139 | Eggplant |
| MAFF211280 | Eggplant |
| MAFF211533 | Eggplant |
| MAFF211468 | Chili pepper |
| MAFF211516 | Bell pepper and sweet green pepper |
| MAFF311101 | Bell pepper and sweet green pepper |
| MAFF311102 | Bell pepper and sweet green pepper |
| MAFF211479 | Ginger |
| MAFF211471 | Ginger |
| MAFF211483 | Ginger |
| MAFF211484 | Ginger |
| MAFF211486 | Ginger |
| MAFF211272 | Curcuma |
| MAFF211276 | Curcuma |
| MAFF211278 | Curcuma |
| MAFF211490 | Myoga ginger |
| MAFF211492 | Myoga ginger |
| MAFF211497 | Myoga ginger |
| MAFF211476 | Ginger |
| MAFF211414 | Potato |
| MAFF211429 | Potato |
| MAFF301558 | Potato |

Example 5

Evaluation of Infection Cycle by One-Step Growth Method

Figure 7:
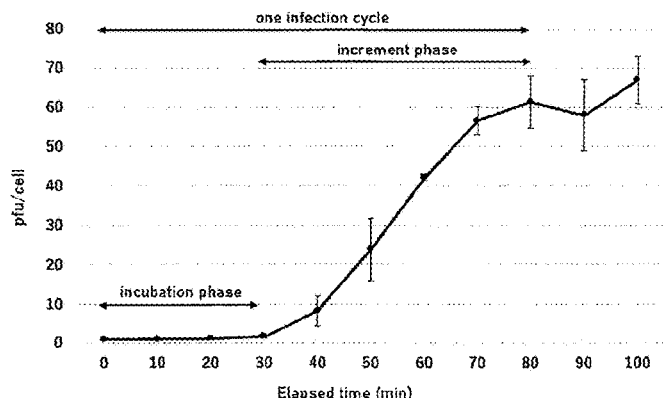
FIG. 7 shows one infection cycle of RKP181 (mean±SD (N=3)).

After mixing 990 μL of a culture solution of *Ralstonia solanacearum* strain MAFF730131 cultured to $OD_{600}$ of 0.15 in CPG medium and 10 μL of a RKP181 phage solution ($2 \times 10^{10}$ pfu/mL), the mixture was left still at room temperature to adsorb the bacterium and the phage. After 10 minutes, the mixture was centrifuged at 5,000×g for 10 minutes, and the supernatant was collected. Then, the plaque assay was conducted, and the number of adsorbed phages was calculated. The precipitates were re-suspended in 1 mL of CPG medium, and 150 μL was then added to 29, 850 μL of CPG medium, followed by culturing with shaking at 28° C. For 100 minutes after starting culturing with shaking, a 10 μL sample was taken every 10 minutes and mixed with 990 μL of CPG medium. After mixing, a serial dilution was prepared according to the need, and 10 μL was taken immediately, added to 250 μL of a culture solution of strain MAFF730131 which was adjusted to $OD_{600}$ of 0.22 to 0.24 and stirred. The total volume thereof was added immediately to top agar, mixed and then layered onto CPG medium. The number of formed plaques was counted, and potency was calculated. From the potency and the adsorbed phage numbers at the each time point, the phage number generated in one infection cycle (burst size) was calculated. The results are shown in FIG. 7 and summarized in Table 7.

TABLE 7

| Latent Period | Rise Period | Infection Cycle | Burst Size |
|---|---|---|---|
| 30 minutes | 50 minutes | 80 minutes | 61 ± 7 pfu |

18

From the above results, it was found that the latent period of RKP181 is 30 minutes and that the infection cycle is 80 minutes. It was also found that the phage number generated in one infection cycle is 6117 pfu.

Example 6

Figure 8:
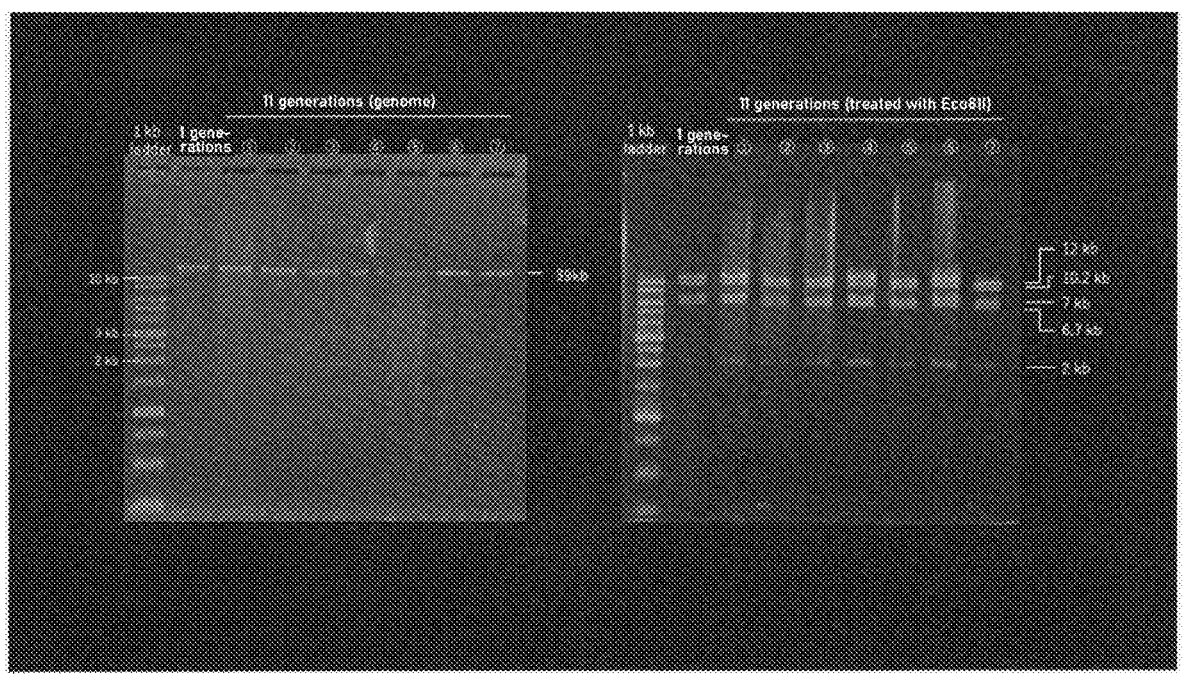
FIG. 8 shows the genetic stability of RKP181 after passage amplification (the left is the full genome length, and the right is after cleavage with the restriction enzyme Eco81I).

Genetic Stability:

RKP181 was amplified by passaging for 10 generations, and seven plaques were isolated. The genomes were prepared after amplifying the isolated seven phages for one more generation, and the genome sizes were determined by the electrophoresis (FIG. 8: left). Moreover, the prepared genomes were treated with Eco81I restriction enzyme. The restriction patterns were examined and observed to be consistent with the matters described in Example 1 above, and thus RKP181 was found to be genetically stable (FIG. 8: right).

Example 7

Control Test:

A $1 \times 10^9$ pfu/mL phage solution in a volume of 5 mL was poured to the roots of seedlings on a cell seedling tray (10 seedlings) of a large tomato variety, Sekaiichi. The control group (10 seedlings) was not treated. After six days, the seedlings were planted in pots, and 5 mL of a bacterial culture solution of strain MAFF730131 which was adjusted to $OD_{660}$=0.1 (corresponding to about $1 \times 10^8$ cfu/mL) was poured to the roots of the seedlings. Then, observation was continued for 22 days. The results are shown in Table 8.

TABLE 8

| | | Day 13 | | Day 20 | | Day 22 | |
|---|---|---|---|---|---|---|---|
| | | | Control Value | | Control Value | | Control Value |
| Without | Incidence Rate | 40 | — | 50 | — | 60 | — |
| Treatment | Disease Severity | 35 | | 50 | | 60 | |
| RKP181 | Incidence Rate | 20 | 50 | 30 | 40 | 30 | 50 |
| Treatment | Disease Severity | 20 | | 30 | | 30 | |

On the 22nd day after the bacterium inoculation, six of the 10 plants withered in the phage-untreated group, and four plants were healthy. On the other hand, in the RKP181 phage-treated group, withering was limited to three of the 10 plants, and seven plants were healthy, with the control value of 50. Thus, the control property of the RKP181 phage was observed.

Example 8

Preparation of Bacterial Wilt DISEASE Control Agent:

Bacteriophage RKP181 separated in Example 1 was adjusted to potency of $1 \times 10^9$ pfu/ml, and a bacterial wilt disease control agent was thus obtained.

INDUSTRIAL APPLICABILITY

The bacteriophage of the invention can be used for controlling bacterial wilt,

The invention claimed is:

1. An engineered bacteriophage comprising a tail fiber protein comprising a host recognition site comprising the amino acid sequence of SEQ ID NO: 1.

2. The bacteriophage of claim 1, wherein the host recognition site is produced by inserting an exogenous host recognition site comprising SEQ ID NO: 1.

3. The bacteriophage of claim 1, wherein the host recognition site is produced by modifying or mutating genomic DNA of the bacteriophage to produce the host recognition site comprising SEQ ID NO: 1.

4. The bacteriophage of claim 1 that is RKP181 which is described by deposit NITE BP-03186.

5. The bacteriophage of claim 1, which belongs to family Podoviridae of order Caudovirales of Group I.

6. The bacteriophage of claim 1, which has a head diameter in a range of from 30 to 90 nm, a tail length in a range of from 5 to 30 nm, and a width in a range of from 5 to 20 nm, has a double-stranded genome, has a genome size in a range of from 6,000 to 280,000 bp, has a GC content in a range of from 55 to 75% and comprises from 10 to 330 genes, wherein genomic DNA of the bacteriophage is digested into fragments by restriction enzyme Eco81I.

7. The bacteriophage of claim 1 that further comprises a gene encoding lysozyme or type II holin.

8. The bacteriophage of claim 1 that further comprises a circular or linear genome.

9. The bacteriophage of claim 1 that infects *Ralstonia solanacearum*.

10. The bacteriophage of claim 9, wherein the *Ralstonia solanacearum* is strain MAFF107624, strain MAFF211266, strain MAFF211270, strain MAFF211543, strain MAFF301859, strain MAFF311644, strain MAFF730103, strain MAFF730131, strain MAFF302745, strain MAFF311632, strain MAFF211536, strain MAFF331041, strain MAFF730139, strain MAFF211280, strain MAFF211533, strain MAFF211468, strain MAFF211516, strain MAFF311101, strain MAFF311102, strain MAFF211479, strain MAFF211471, strain MAFF211483, strain MAFF211484, strain MAFF211486, strain MAFF211272, strain MAFF211276, strain MAFF211278, strain MAFF211490, strain MAFF211492, strain MAFF211497, strain MAFF211476, strain MAFF211414, strain MAFF211429, or strain MAFF301558.

11. A composition comprising the bacteriophage of claim 9 and a pharmacologically and botanically acceptable protein stabilizer.

12. The composition of claim 11 which suppresses wilt by *Ralstonia solanacearum* when applied to a plant.

13. The composition of claim 11, wherein the bacteriophage is present at a concentration ranging from $10^3$ to $10^{12}$ pfu/mL.

14. A method for suppressing bacterial wilt disease comprising contacting a plant or plant growth medium with the bacteriophage of claim 9.

15. The method of claim 14, wherein the plant is infected by *Ralstonia solanacearum*.

16. The method of claim 14, wherein the plant is infected by *Ralstonia solanacearum* strain MAFF107624, strain MAFF211266, strain MAFF211270, strain MAFF211543, strain MAFF301859, strain MAFF311644, strain MAFF730103, strain MAFF730131, strain MAFF302745, strain MAFF311632, strain MAFF211536, strain MAFF331041, strain MAFF730139, strain MAFF211280, strain MAFF211533, strain MAFF211468, strain MAFF211516, strain MAFF311101, strain MAFF311102, strain MAFF211479, strain MAFF211471, strain MAFF211483, strain MAFF211484, strain MAFF211486, strain MAFF211272, strain MAFF211276, strain MAFF211278, strain MAFF211490, strain MAFF211492, strain MAFF211497, strain MAFF211476, strain MAFF211414, strain MAFF211429, or strain MAFF301558.

17. The method of claim 14, wherein the plant is a member of Solanaceae, Lamiaceae or Zingiberaceae.

18. The method of claim 14, wherein the plant selected from the group consisting of tomatoes, eggplants, bell peppers, or tobaccos of the family Solanaceae; *Perilla frutescens* var. *crispa* or *Perilla frutescens* of the family Lamiaceae; and ginger, turmeric and curcuma of the family Zingiberaceae.

19. A bacteriophage tail fiber protein comprising a host recognition site for *Ralstonia solanacearum* shown in SEQ ID NO: 1.

20. A base sequence encoding the bacteriophage tail fiber protein of claim 19.

* * * * *